US007756572B1

(12) United States Patent
Fard et al.

(10) Patent No.: US 7,756,572 B1
(45) Date of Patent: Jul. 13, 2010

(54) SYSTEM AND METHOD FOR EFFICIENTLY DISTINGUISHING AMONG CARDIAC ISCHEMIA, HYPOGLYCEMIA AND HYPERGLYCEMIA USING AN IMPLANTABLE MEDICAL DEVICE AND AN EXTERNAL SYSTEM

(75) Inventors: Mohssen Fard, Woodland Hills, CA (US); Xiaoyi Min, Thousand Oaks, CA (US); Peter Boileau, Valencia, CA (US); Jong Gill, Valencia, CA (US); Bing Zhu, Sunnyvale, CA (US); Jay Snell, Studio City, CA (US); Laleh Jalali, Moorpark, CA (US); Josh Reiss, Kirkland, WA (US); Gene Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 590 days.

(21) Appl. No.: 11/740,175

(22) Filed: Apr. 25, 2007

Related U.S. Application Data

(63) Continuation-in-part of application No. 11/043,612, filed on Jan. 25, 2005, now Pat. No. 7,502,644.

(51) Int. Cl.
*A61B 5/0468* (2006.01)
(52) U.S. Cl. ...................... 600/517; 600/516
(58) Field of Classification Search ............ 600/516, 600/517
See application file for complete search history.

(56) References Cited

U.S. PATENT DOCUMENTS

| 4,731,051 A | 3/1988 | Fischell |
| 4,759,366 A | 7/1988 | Callaghan |
| 4,947,845 A | 8/1990 | Davis |
| 5,113,869 A | 5/1992 | Nappholz et al. |
| 5,135,004 A | 8/1992 | Adams et al. |
| 5,148,812 A | 9/1992 | Verrier et al. |
| 5,199,428 A | 4/1993 | Obel et al. |

(Continued)

FOREIGN PATENT DOCUMENTS

EP 0472411 A1 2/1992

(Continued)

OTHER PUBLICATIONS

Blendea, Mihaela C., MD, PhD, et al, "Heart Disease in Diabetic Patients" Current Diabetes Reports, 2003; vol. 3. pp. 223-229.

(Continued)

*Primary Examiner*—Michael Kahelin

(57) ABSTRACT

Techniques are described for efficiently detecting and distinguishing among cardiac ischemia, hypoglycemia or hyperglycemia based on intracardiac electrogram (IEGM) signals. In one example, a preliminary indication of an episode of cardiac ischemia is detected based on shifts in ST segment elevation within the IEGM. In response, the implanted device then records additional IEGM data for transmission to an external system. The external system analyzes the additional IEGM data to confirm the detection of cardiac ischemia using a more sophisticated analysis procedure exploiting additional detection parameters. In particular, the external system uses detection parameters capable of distinguishing hypoglycemia, hyperglycemia and hyperkalemia from cardiac ischemia, such as QTmax and QTend intervals. Alternatively, the more sophisticated analysis procedure may be performed by the device itself, if it is so equipped. Other examples described herein pertain instead to the detection of atrial fibrillation.

18 Claims, 24 Drawing Sheets

U.S. PATENT DOCUMENTS

| | | | |
|---|---|---|---|
| 5,203,326 | A | 4/1993 | Collins |
| 5,313,953 | A | 5/1994 | Yomtov et al. |
| 5,328,460 | A | 7/1994 | Lord et al. |
| 5,365,426 | A | 11/1994 | Siegel et al. |
| 5,400,795 | A | 3/1995 | Murphy et al. |
| 5,425,749 | A | 6/1995 | Adams |
| 5,520,191 | A | 5/1996 | Karlsson et al. |
| 5,720,295 | A | 2/1998 | Greenhut et al. |
| 5,741,211 | A | 4/1998 | Renirie et al. |
| 5,785,660 | A | 7/1998 | van Lake et al. |
| 5,792,065 | A | 8/1998 | Xue et al. |
| 5,891,047 | A | 4/1999 | Lander et al. |
| 5,960,797 | A | 10/1999 | Kramer et al. |
| 6,016,443 | A | 1/2000 | Ekwall et al. |
| 6,021,350 | A | 2/2000 | Mathson |
| 6,038,469 | A | 3/2000 | Karlsson et al. |
| 6,108,577 | A | 8/2000 | Benser |
| 6,112,116 | A | 8/2000 | Fischell et al. |
| 6,115,628 | A | 9/2000 | Stadler et al. |
| 6,128,526 | A | 10/2000 | Stadler et al. |
| 6,233,486 | B1 | 5/2001 | Ekwall et al. |
| 6,249,705 | B1 | 6/2001 | Snell |
| 6,256,538 | B1 | 7/2001 | Ekwall |
| 6,264,606 | B1 | 7/2001 | Ekwall et al. |
| 6,272,379 | B1 | 8/2001 | Fischell et al. |
| 6,361,503 | B1 | 3/2002 | Starobin et al. |
| 6,377,852 | B1 | 4/2002 | Bornzin et al. |
| 6,381,493 | B1 | 4/2002 | Stadler et al. |
| 6,501,983 | B1 | 12/2002 | Natarajan et al. |
| 6,572,542 | B1 | 6/2003 | Houben et al. |
| 6,622,045 | B2 | 9/2003 | Snell et al. |
| 6,731,985 | B2 | 5/2004 | Poore et al. |
| 7,010,345 | B2 | 3/2006 | Hill et al. |
| 7,016,720 | B2 | 3/2006 | Kroll |
| 7,029,443 | B2 | 4/2006 | Kroll |
| 7,076,300 | B1 | 7/2006 | Kroll et al. |
| 7,096,064 | B2 | 8/2006 | Deno et al. |
| 7,103,412 | B1 | 9/2006 | Kroll |
| 7,142,911 | B2 | 11/2006 | Boileau et al. |
| 7,272,436 | B2 | 9/2007 | Gill et al. |
| 7,297,114 | B2 | 11/2007 | Gill et al. |
| 2002/0095095 | A1* | 7/2002 | Callahan et al. ............ 600/516 |
| 2002/0143266 | A1 | 10/2002 | Bock |
| 2002/0143372 | A1 | 10/2002 | Snell et al. |
| 2003/0158492 | A1* | 8/2003 | Sheldon et al. ............ 600/508 |
| 2004/0077962 | A1 | 4/2004 | Kroll |
| 2004/0078065 | A1 | 4/2004 | Kroll |
| 2004/0138716 | A1 | 7/2004 | Kon et al. |
| 2004/0249420 | A1 | 12/2004 | Olson et al. |
| 2005/0177049 | A1* | 8/2005 | Hardahl et al. ............ 600/509 |
| 2005/0288725 | A1 | 12/2005 | Hettrick et al. |
| 2006/0167365 | A1 | 7/2006 | Bharmi |
| 2006/0167517 | A1 | 7/2006 | Gill et al. |
| 2006/0167518 | A1 | 7/2006 | Gill et al. |
| 2006/0167519 | A1 | 7/2006 | Gill et al. |
| 2006/0247685 | A1 | 11/2006 | Bharmi |

FOREIGN PATENT DOCUMENTS

| | | |
|---|---|---|
| EP | 0867146 A1 | 9/1998 |
| EP | 0867146 B1 | 9/1998 |
| EP | 1419731 A1 | 5/2004 |
| EP | 1419731 B1 | 5/2004 |
| EP | 0939602 B1 | 9/2004 |
| WO | WO97/15227 | 5/1997 |
| WO | WO 2006/081336 A2 | 8/2006 |

OTHER PUBLICATIONS

Eckert, Bodil et al. "Hypoglycaemia Leads to an Increased QT Interval in Normal Men," Clinical Physiology, vol. 18, No. 6 (1998), pp. 570-575.

Heller, Simon R, "Abnormalities of the Electrocardiogram during Hypoglycemia: The Cause of the Dead in Bed Syndrome?" Int. J. Clin. Pract. Suppl. No. 129 (Jul. 2002), pp. 27-32.

Jones, Timothy W. et al., "Mild Hypoglycemia and Impairment of Brain Stem and Cortical Evoked Potentials in Healthy Subjects," Diabetes 39:1550-1555 (Dec. 1990).

Landstedt-Hallin, L. et al., "Increased QT Dispersion During Hypoglycaemia During Hypoglycaemia in Patients with Type 2 Diabetes Mellitus," Journal of Internal Medicine (1999); 246:299-307.

Malmberg, Klas for the DIGAMI Study Group, "Prospective Randomised Study of Intensive Insulin Treatment on Long-Term Survival After Acute Myocardial Infarction in Patients with Diabetes Mellitus", BMJ, May 24, 1997; vol. 314, pp. 1512-1515.

Robinson, R.T.C.E. et al. "Changes in Cardiac Repolarization During Clinical Episodes of Nocturnal Hypoglycaemia in Adults with Type 1 Diabetes," Diabetologia, vol. 47 (2004), pp. 312-315.

Peterson, Karl-Georg et al., "Regulation of Serum Potassium During Insulin-Induced Hypoglycemia," Diabetes 31:615-617 (Jul. 1982).

Yanowitz, Frank G MD, Prof. of Medicine, Univ. of Utah School of Medicine, "Lesson X. ST Segment Abnormalities," The Alan E. Lindsay—ECG Learning Center—In Cyberspace, 5 pages.

Harris, ND, et al., "Can Changes in QT Interval be used to Predict the Onset of Hypoglycemia in Type 1 Diabetes?" Computers in Cardiology 2000;27:375-378.

Markel, A. et al, "Hypoglycaemia-induced ischaemic ECG changes." Presse Med., Jan. 22, 1994, 23(2):78-9.

Okin, Peter M., et al, "Electrocardiographic Repolarization Complexity and Abnormality Predict All-Cause and Cardiovascular Mortality in Diabetes," Diabetes, Feb. 2004; 53:434-440.

Rana, Bushra S., et al., "Relation of QT Interval Dispersion to the Number of Different Cardiac Abnormalities in Diabetes Mellitus," Am J Cardiol 2002;90:483-487.

NonFinal Office Action, mailed Jan. 10, 2007: Related U.S. Appl. No. 11/043,780.

Notice of Allowance, mailed May 9, 2007: Related U.S. Appl. No. 11/043,780.

Notice of Allowance, mailed Mar. 7, 2007: Related U.S. Appl. No. 11/043,804.

European Search report, mailed Jan. 9, 2006: Related Application EP06719544.6.

NonFinal Office Action, mailed Jan. 23, 2008—Related U.S. Appl. No. 11/043,612.

NonFinal Office Action, mailed Jul. 14, 2008—Related U.S. Appl. No. 11/043,612.

NonFinal Office Action, mailed Mar. 25, 2008—Related U.S. Appl. No. 11/117,624.

NonFinal Office Action, mailed Jun. 12, 2008—Related U.S. Appl. No. 11/117,624.

NonFinal Office Action, mailed Sep. 10, 2008—Related U.S. Appl. No. 11/127,370.

Steinhaus, Bruce M. et al., "The Information Content of the Cardiac Electrogram at the Stimulus Site," Annual International Conference of the IEEE Engineering in Medicine and Biology Society. 1990;12(2):0607-0609.

* cited by examiner

SYSTEM AND METHOD FOR EFFICIENTLY DISTINGUISHING AMONG CARDIAC ISCHEMIA, HYPOGLYCEMIA AND HYPERGLYCEMIA USING AN IMPLANTABLE MEDICAL DEVICE AND AN EXTERNAL SYSTEM

CROSS REFERENCE TO RELATED APPLICATIONS

This application is a continuation-in-part of U.S. patent application Ser. No. 11/043,612, filed Jan. 25, 2005, now U.S. Pat. No. 7,502,644 entitled "System and Method for Distinguishing Among Cardiac Ischemia, Hypoglycemia and Hyperglycemia using an Implantable Medical Device" and is related to U.S. Patent Applications: 1) Ser. No. 11/043,780, entitled "System and Method for Distinguishing among Cardiac Ischemia, Hypoglycemia and Hyperglycemia using an Implantable Medical Device"; and 2) Ser. No. 11/043,804, also entitled "System and Method for Distinguishing among Cardiac Ischemia, Hypoglycemia and Hyperglycemia using an Implantable Medical Device", all of which are incorporated by reference herein.

FIELD OF THE INVENTION

The invention generally relates to implantable medical devices such as pacemakers and implantable cardioverter/defibrillators (ICDs) and to external devices for use therewith such as external programmer devices and, in particular, to techniques for detecting cardiac ischemia, hypoglycemia, hyperglycemia and other medical conditions using such devices.

BACKGROUND

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death both in the United States and worldwide. In other cases, although the AMI itself is not fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically, resulting in little or no net flow of blood from the heart to the brain and other organs. Indeed, serious episodes of cardiac ischemia (referred to herein as acute myocardial ischemia) typically result in either a subsequent AMI or VF, often within one to twenty-four four hours, sometimes within only a half an hour or less. Accordingly, it would be highly desirable to provide a technique for reliably detecting acute myocardial ischemia so that the victim may be warned and medical attention sought. If properly warned, surgical procedures may be implemented to locate and remove the growing arterial blockage or anti-thrombolytic medications may be administered. At the very least, advanced warning would allow the victim to cease activities that might result in a fatal accident. Moreover, in many cases, AMI or VF is triggered by strenuous physical activities and so advanced warning would allow the victim to cease such activities, possibly preventing AMI or VF from occurring.

Many patients at risk of cardiac ischemia have pacemakers, ICDs or other medical devices implanted therein. Accordingly, techniques have been developed for detecting cardiac ischemia using implanted medical devices. In particular, techniques have been developed for analyzing intracardiac electrogram (IEGM) signals in an effort to detect cardiac ischemia. See, as examples, the following U.S. Pat. Nos. 5,113,869 to Nappholz; 5,135,004 to Adams et al.; 5,199,428 to Obel et al.; 5,203,326 to Collins; 5,313,953 to Yomtov et al; 6,501,983 to Natarajan, et al.; 6,016,443, 6,233,486, 6,256,538, and 6,264,606 to Ekwall; 6,021,350 to Mathson; 6,112,116 and 6,272,379 to Fischell et al; 6,128,526, 6,115,628 and 6,381,493 to Stadler et al; and 6,108,577 to Benser. Most IEGM-based ischemia detection techniques seek to detect ischemia by identifying changes in the elevation of the ST segment of the IEGM that occur during cardiac ischemia. The ST segment represents the portion of the cardiac signal between ventricular depolarization (also referred to as an R-wave or QRS complex) and ventricular repolarization (also referred to as a T-wave). Herein, the ST segment elevation pertains to the amplitude of the ST segment relative to some isoelectric baseline and hence can be positive or negative. A change in the ST segment elevation is referred to herein as an ST segment deviation, i.e. ST segment deviation refers to a change in ST segment elevation relative to a historical elevation baseline. The QRS complex usually follows an atrial depolarization (also referred to as a P-wave.) Note that QRS complexes can also be regarded as being representative of the "activation" of the ventricles; whereas T-waves can also be regarded as being representative of "deactivation" of the ventricles. These alternative terms are used herein for generality where appropriate.

A significant concern with any cardiac ischemia detection technique that relies on changes in the ST segments is that systemic influences within the patient can alter the ST segment. For example, hypoglycemia (low blood sugar levels) and hyperglycemia (high blood sugar levels) can both affect ST segment deviation. In addition, electrolyte imbalance, such as hypokalemia (low potassium levels) or hyperkalemia (high potassium levels) can affect the ST segment. Certain anti-arrhythmic drugs can also affect the ST-segment. Techniques for detecting and discerning between electrocardiographic effects of cardioactive drugs are described in U.S. Pat. No. 7,142,911, to Boileau, et al. Nov. 28, 2006, which is incorporated by reference herein. In addition to systemic influences, acute pericarditis, pulmonary embolism and the acute onset of conduction disorders (for example left or right bundle branch block) can also cause dramatic changes in the ST-segment over the short term. Ventricular pacing alters the pattern of ventricular depolarization and repolarization. Therefore the paced QRST complex or "evoked response" following a ventricular pacing stimulus typically has a morphology much different than an intrinsic QRS complex. The ST segment elevation of a paced QRST complex may be different than the ST elevation following an intrinsic QRS complex. Also, ischemia may not manifest as ST segment elevation in a paced QRST complex as readily as it might in an intrinsic QRST complex.

Accordingly, alternative techniques for detecting cardiac ischemia have been developed, which do not rely on ST segment elevation. One such technique is set forth in U.S. patent application Ser. No. 10/603,429, entitled "System and Method for Detecting Cardiac Ischemia Using an Implantable Medical Device," of Wang et al., filed Jun. 24, 2003, which is incorporated by reference herein. Rather than examine the ST segment, the technique of Wang et al. instead examines post-T-wave segments, i.e. that portion of the cardiac signal immediately following the T-wave. In one example, the onset of cardiac ischemia is identified by detecting a sharp falling edge within post-T-wave signals. A warning is then provided to the patient. The warning preferably includes both a perceptible electrical notification signal applied directly to subcutaneous tissue and a separate warning signal delivered via short-range telemetry to a handheld warning device external to the patient. After the patient feels the internal warning signal, he or she holds the handheld device near the chest to receive the short-range telemetry signal, which provides a textual warning. The handheld warning device thereby provides confirmation of the warning to the patient, who may be otherwise uncertain as to the reason for the internally generated warning signal. Another technique for detecting cardiac ischemia based on T-waves is set forth in U.S. patent application Ser. No. 10/603,398, entitled "System and Method for Detecting Cardiac Ischemia based on T-Waves using an Implantable Medical Device," of Min et al., filed Jun. 24, 2003, which is also incorporated by reference herein. With the technique of Min et al., cardiac ischemia is detected based either on the total energy of the T-wave or on the maximum slope of the T-wave. Again, if ischemia is detected, a warning signal is provided to the patient.

Hence, various cardiac ischemia detection techniques have been developed that exploit T-waves. Although these techniques are effective, it is desirable to provide still other T-wave-based ischemia detection techniques. It is also desirable to provide techniques that exploit deviations in the ST segment as well as changes in T-waves to provide further improvements in cardiac ischemia detection. In particular, it is highly desirable to identify particular changes in T-waves that can be used to distinguish deviations in the ST segment caused by cardiac ischemia from changes caused by hypoglycemia or hyperglycemia or other systemic affects such as hyperkalemia so as to improve the reliability and specificity of ST segment-based ischemia detection. Various techniques originally described in the parent patent application cited above (and described herein below as well) were provided to satisfy these needs. Briefly, the parent application set forth techniques for detecting ischemia based on IEGM signals using an implanted device. Ischemia is detected based on a shortening of the interval between the QRS complex and the end of a T-wave (referred to as a QTmax interval), alone or in combination with a change in ST segment elevation. Alternatively, ischemia is detected based on a change in ST segment elevation combined with minimal change in the interval between the QRS complex and the end of the T-wave (referred to as a QTend interval).

Although the detection of cardiac ischemia is of particular importance since an ischemia may be a precursor to a potentially fatal AMI or VF, it is also desirable to detect other conditions such as hypoglycemia or hyperglycemia as especially applicable to diabetics, and hyperkalemia as especially applicable to patients with kidney failure and heart failure patients on potassium-sparing diuretics, so as to provide suitable warning signals and still other aspects of the invention are directed to that end. Diabetic patients, particular, need to frequently monitor blood glucose levels to ensure that the levels remain within acceptable bounds and, for insulin dependent diabetics, to determine the amount of insulin that must be administered. Conventional techniques for monitoring blood glucose levels, however, leave much to be desired. One conventional technique, for example, requires that the patient draw blood, typically by pricking the finger. The drawn blood is then analyzed by a portable device to determine the blood glucose level. The technique can be painful and therefore can significantly discourage the patient from periodically checking blood glucose levels. Moreover, since an external device is required to analyze the blood, there is the risk that the patient will neglect to keep the device handy, preventing periodic blood glucose level monitoring. For insulin-dependent diabetics, failure to properly monitor blood glucose levels can result in improper dosages of insulin causing, in extreme cases, severe adverse health consequences such as a ketoacidotic diabetic coma, which can be fatal. Accordingly, there is a significant need to provide a reliable hypo/hyperglycemia detection technique, which does not rely on the patient to monitoring his or her own glucose levels and which does not require an external analysis device.

In view of the many disadvantages of conventional external blood glucose monitoring techniques, implantable blood glucose monitors have been developed, which included sensors for mounting directly within the blood stream. However, such monitors have not achieved much success as the glucose sensors tend to clog over very quickly. Thus, an implantable device that could continually and reliably measure blood glucose levels without requiring glucose sensors would be very desirable. Moreover, as with any implantable device, there are attended risks associated with implanting the blood glucose monitor, such as adverse reactions to anesthetics employed during the implantation procedure or the onset of subsequent infections. Hence, it is desirable to provide for automatic hypo/hyperglycemia detection using medical devices that would otherwise need to be implanted anyway, to thereby minimize the risks associated with the implantation of additional devices. In particular, for patients already requiring implantation of a cardiac stimulation device, such as a pacemaker or ICD, it is desirable to exploit features of electrical cardiac signals, particularly ST segments and T-waves, for use in detecting hypo/hyperglycemia and still other aspects of the invention are directed to that end. Similarly, hyperkalemia, which can lead to life-threatening arrhythmias, is a risk for patients who are also implanted with a cardiac stimulation device. This is because kidney failure often occurs secondary to heart failure, and also because heart-failure patients may be taking potassium-sparing diuretics. It would be desirable to exploit features of cardiac signals to warn of a possibly life-threatening rise in potassium levels which could signal new onset kidney failure, an urgent need for dialysis and/or change in medication. Various techniques originally described in the parent patent application (and also described herein below) were also provided to satisfy these needs. Briefly, the parent application set forth techniques for detecting hypoglycemia based on a change in ST segment elevation along with a lengthening of either QTmax or QTend. Hyperglycemia is detected based on a change in ST segment elevation along with minimal change in QTmax and in QTend. By exploiting QTmax and QTend in combination with ST segment elevation, changes in ST segment elevation caused by hypo/hyperglycemia can be properly distinguished from changes caused by ischemia.

Although the techniques of the parent application are effective, room for further improvement remains. In particular, the analysis needed to process QTmax and QTend intervals, in addition to ST segment elevation, can be burdensome on the implanted device, consuming memory and processing resources. Accordingly, it would be desirable to provide techniques for more efficiently detecting cardiac ischemia and distinguishing it from hypoglycemia and hyperglycemia that reduce at least some of this processing burden on the implanted device. Further, it would be desirable to apply these more efficient detection techniques to the detection of other medical conditions as well, particularly atrial fibrillation (AF).

SUMMARY

In accordance with a first illustrative embodiment, ST segment elevation is detected within electrical cardiac signal data (such as IEGM data) sensed by an implanted device. A preliminary indication of an episode of cardiac ischemia is then made by the implanted device based on ST segment elevation. In response, the implanted device then senses additional cardiac signal data. The additional cardiac signal data is analyzed to confirm the detection of cardiac ischemia using at least one ischemia detection parameter other than (or in addition to) ST segment elevation, such as QTmax and QTend intervals. As such, the technique provides a two-tier or two-stage ischemia detection procedure, with the second stage employing a more sophisticated detection technique.

In one example, a preliminary indication of cardiac ischemia is made by the implanted device based on an ST segment shift detected using sets of about eight to sixteen heartbeats. Once the preliminary indication is made, the implanted device starts recording additional cardiac signal data (preferably about four hours worth of IEGM data) and the patient is notified of a possible medical condition using, for example, an implanted "tickle" warning device. The patient then uses a transtelephonic relay system to transmit the additional cardiac signal data from the implanted device to a centralized computing system, which analyzes the data to confirm the detection of cardiac ischemia based on both ST segment elevations and QTmax and QTend intervals. The centralized system preferably also distinguishes hypo/hyperglycemia and hyperkalemia from cardiac ischemia. If any of these medical conditions is confirmed by the centralized system, the patient's physician or other appropriate clinician is notified to take corrective action. In this manner, the implanted device need not be equipped to perform the more sophisticated analysis involving QTmax and QTend intervals, thus reducing processing and memory requirements within the device itself. Alternatively, the external analysis is instead performed by an external programmer, which receives the additional cardiac signal data directly from the implanted device, typically under the supervision of a clinician.

In another example, the implanted device is instead equipped to perform the additional analysis. That is, once a preliminary indication of cardiac ischemia is detected, the implanted device then analyzes additional cardiac signal data to confirm the detection of ischemia based on both ST segment elevation and QTmax and QTend intervals. The device preferably also distinguishes other potential causes of changes in ST segment elevation from cardiac ischemia, such as hyper/hypoglycemia or hyperkalemia. If any of these medical conditions is confirmed by the device, the patient is warned of the medical condition. The patient then preferably uses the transtelephonic relay system to transmit the warning (as well as information pertaining to the analysis of the cardiac signal data up on which the warning was based) to the patient's physician or other clinician, who can then take corrective action. Thus, in this example, although the device is equipped to perform the more sophisticated analysis based on a combination of ST segment elevations, QTmax and QTend intervals, it does not routinely do so. The more sophisticated analysis is only performed by the device if a preliminary detection of cardiac ischemia is first made based solely on ST segment elevations. Hence, the device is not burdened with the need to continuously track and analyze QTmax and QTend intervals, thus saving power and other device resources.

The following table summarizes changes in the ST segment, QTmax and QTend in response to cardiac ischemia, hypoglycemia, and hyperglycemia that are exploited in various embodiments of the invention.

TABLE I

|  | ST Segment | QTmax | QTend |
| --- | --- | --- | --- |
| Ischemia | Significant deviation | Shortens | Little or no change |
| Hypoglycemia | Significant deviation | Lengthens | Lengthens |
| Hyperglycemia | Significant deviation | Little or no change | Little or no change |
| Hyperkalemia/ digitalis | Significant deviation | Shortens | Shortens |
| Normal/ cardioactive drugs (other than digitalis) | No significant deviation | May vary with QTend | May vary with QTmax |

Insofar as normal variations in QTmax and QTend are concerned, under normal (i.e. non-ischemic, non-hypoglycemic, non-hyperglycemic and non-hyperkalemic) conditions, QT typically varies with heart rate, autonomic tone, cardioactive drugs, etc. However, under non-ischemic conditions, if QTmax and QTend vary, the two values typically change in lock-step, i.e. QTend-QTmax remains the same. The ST segment elevation does not change significantly under non-ischemic conditions. As noted, ST segment elevation does change due to ischemia, hypo/hyperglycemia, etc. However, the case where ST elevation changes, but QTend stays the same and QTmax shortens appears to be unique to ischemia and hence is useful for detecting ischemia and distinguishing it from other conditions.

In implementations where the implanted device itself performs the more sophisticated analysis to distinguish among cardiac ischemia, hyperglycemia, hypoglycemia and hyperkalemia, the device may also be equipped to automatically deliver therapy in response thereto. In this regard, pacing therapy may be modified in response to the detected medical condition or, if the device is equipped with a drug pump, appropriate medications may be administered. For cardiac ischemia, anti-thrombolytic drugs may be delivered. For hypo/hyperglycemia, insulin may be regulated. In addition, if the device is an ICD, it may be controlled to immediately begin charging defibrillation capacitors upon detection of cardiac ischemia so as to permit prompt delivery of a defibrillation shock, which may be needed if the ischemia triggers VF.

Hence, improved techniques are provided for more efficiently detecting cardiac ischemia, hypoglycemia, hyperglycemia and hyperglycemia and for distinguishing therebetween so as to reduce the processing burdens on the implanted device.

The techniques of the invention may be additionally, or alternatively, applied to the detection of other medical conditions, particularly AF. In one example, the implanted device detects cardiac signal data and detects a preliminary indication of an episode of AF based on the cardiac signal data using a first analysis procedure. In response, additional cardiac signal data is sent to an external system for confirmation. The additional cardiac signal data is then analyzed by the external system to confirm the detection of AF using a second analysis procedure having greater specificity than the first analysis procedure. In one particular example, the implanted device detects possible AF based on atrial rate. The external system confirms the detection of AF based on a more sophisticated morphological analysis of atrial IEGM data.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout. FIGS. 1-15 are primarily directed to describing systems and methods for detecting and distinguishing among cardiac ischemia, hypoglycemia, hyperglycemia and, in some examples, hyperkalemia. These techniques were originally described with the above-cited parent application and are included herein for the sake of completeness. FIGS. 16-24 are primarily directed to describing systems and methods for more efficiently detecting and distinguishing between cardiac ischemia from other potential causes of changes in ST segment elevation by employing a two-tier detection procedure. Systems and methods for efficiently detecting and distinguishing AF are also described in this section.

In the various descriptions herein, the following terms are used:
- a. ST Elevation refers to the amplitude of the ST segment relative to an isoelectric baseline (pre-P-wave or pre-R-wave). (See, e.g., FIG. 7.)
- b. ST Deviation refers a change in ST Elevation over time with respect to a historical baseline. (See, e.g., FIG. 10.)
- c. QTmax and QTend refer to time intervals from the start of the QRS to the peak of the T-wave and to the end of the T-wave, respectively. (See, e.g., FIG. 4 and FIG. 7.)
- d. ΔQTmax and ΔQTmin refer to changes in QTmax and QTend over time with respect to historical baselines. (See, e.g., FIG. 5 and FIG. 8)

Overview of an Exemplary Implantable Device

Figure 1:
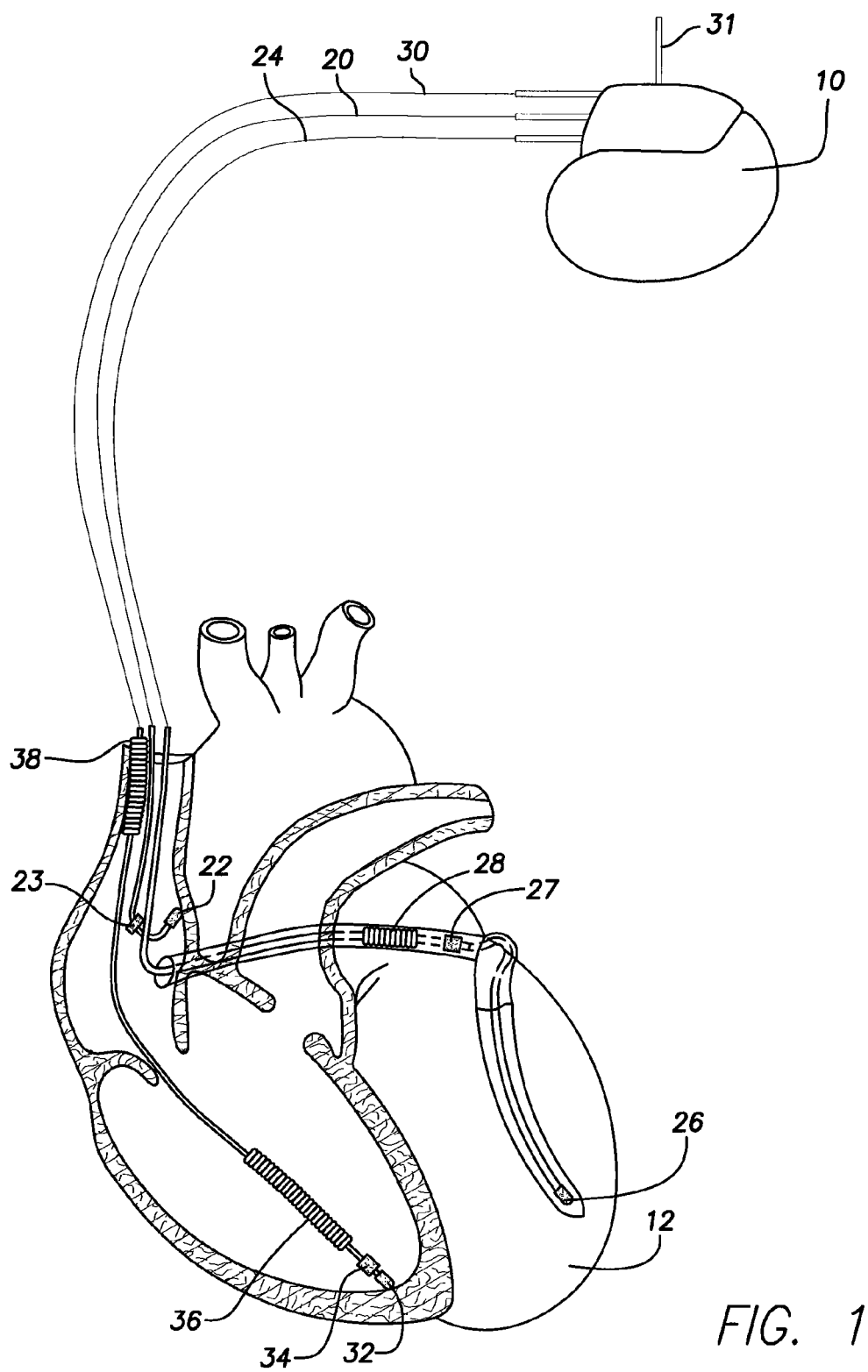
FIG. 1 is a simplified diagram illustrating an implantable stimulation device with at least three leads implanted in the heart of a patient for delivering multi-chamber stimulation and shock therapy.

As shown in FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "tickle warning" signal, an additional electrode 31 is provided in proximity to the device can.

Figure 2:
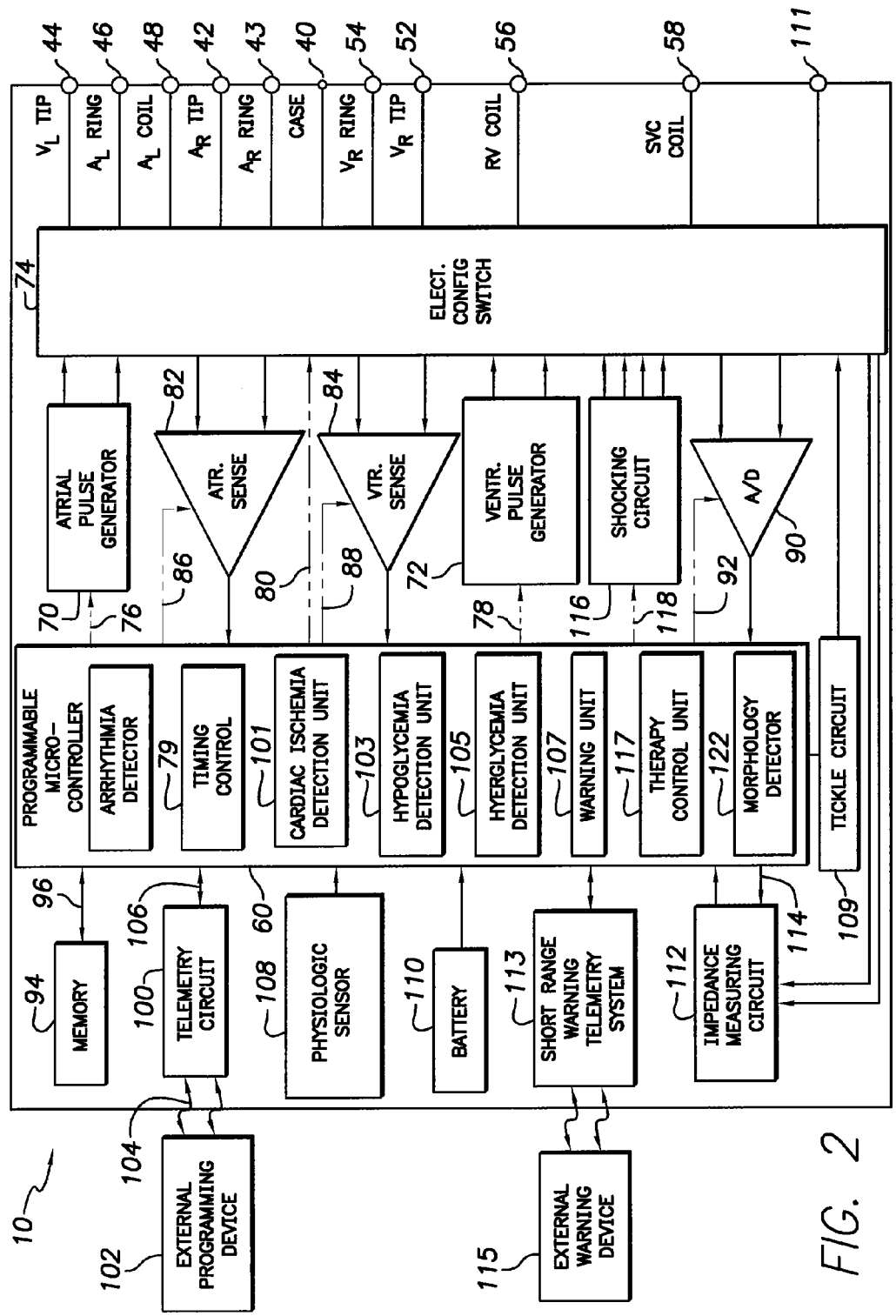
FIG. 2 is a functional block diagram of the implantable cardiac stimulation device of FIG. 1 illustrating basic elements of the stimulation device, particularly illustrating components for detecting cardiac ischemia, hypoglycemia, and hyperglycemia based on various combinations of QTmax, QTend and ST deviation.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. To provide the "tickle warning" signal, an additional terminal 59 is provided for connection to the tickle warning electrode 31 of FIG. 1.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112, which is enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Finally, with regard to FIG. 2, microcontroller 60 includes: a cardiac ischemia detection unit 101 for controlling the detection of episodes of cardiac ischemia; hypoglycemia detection unit 103 for controlling the detection of episodes of hypoglycemia; and a hyperglycemia detection unit 105 for controlling the detection of episodes of hyperglycemia. A warning unit 107 controls delivery of warning signals to the patient indicative of ischemia, hypoglycemia, or hyperglycemia. In particular, warning unit 107 controls a tickle circuit 109 that generates subcutaneous perceptible warning signals via lead 31 (FIG. 1), which is connected via connector 111. Device case electrodes 40 may be used as the return electrode for the tickle warning signal. Thereafter, warning unit 107 controls a short-range telemetry system 113 to transmit warning signals to an external handheld warning device 115 for confirmation. Additionally, a therapy control unit 117 may be provided to control therapy based upon the detection of ischemia, hypoglycemia or hyperglycemia. The operation of these devices will be described below with reference to the remaining figures.

Referring to the remaining figures, flow charts, graphs and other diagrams illustrate the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Cardiac Ischemia Detection Based on QTmax

Figure 3:
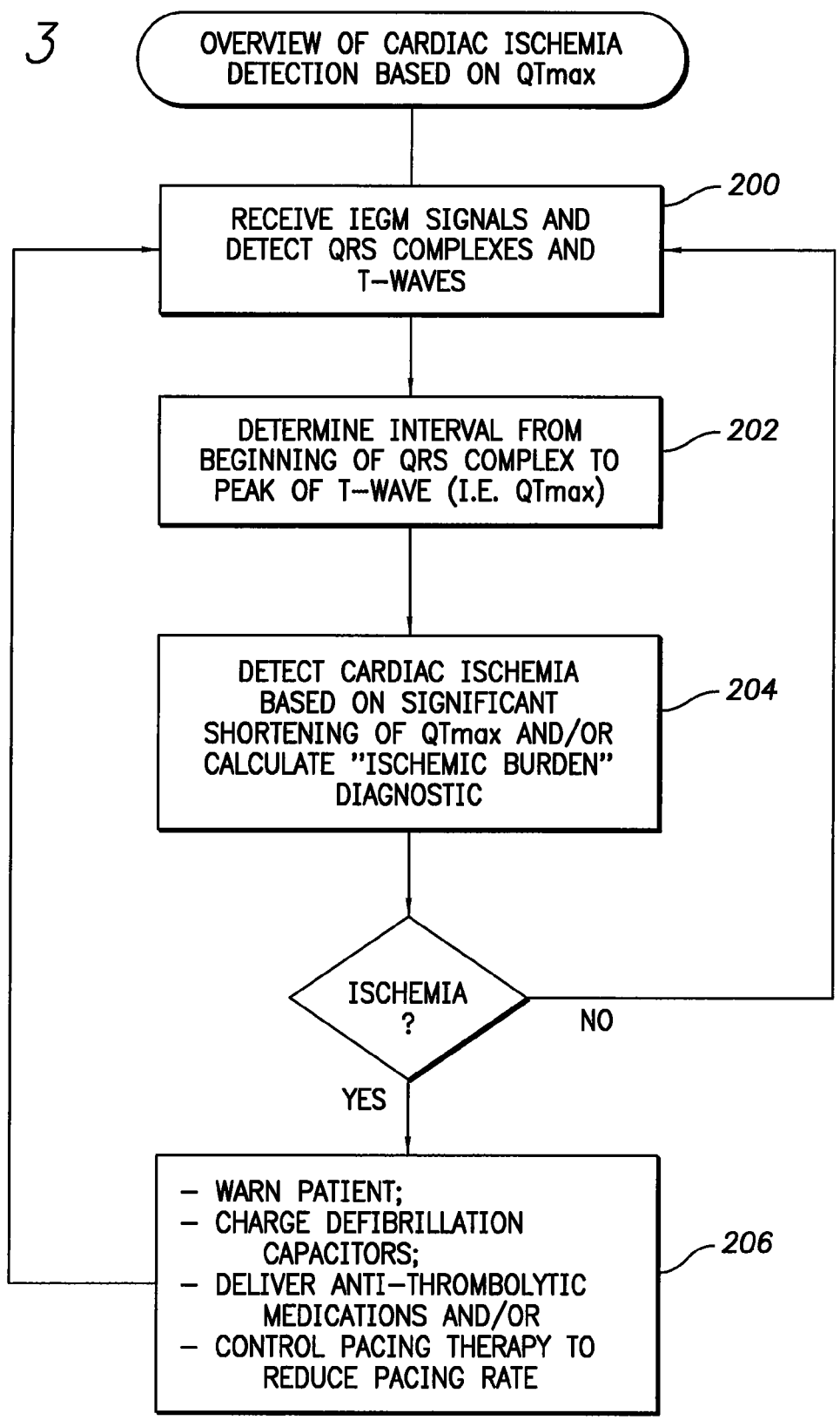
FIG. 3 is a flow chart providing an overview of an exemplary method performed by the device of FIG. 2 for detecting cardiac ischemia based on a reduction in QTmax.

FIG. 3 provides an overview of a QTmax-based cardiac ischemia detection technique performed by the device of FIG. 2. Initially, at step 200, IEGM signals are received and QRS-complexes and T-waves are identified therein. Then, the interval from the beginning of the QRS complex to the peak or maximum absolute amplitude of the T-wave is calculated, at step 202. This interval is referred to herein as QTmax. The Q wave of the QRS complex may be identified as the point within the QRS complex where the IEGM signal exceeds a threshold value set based on the maximum amplitude of the QRS complex itself. The maximum of the T-wave may be identified as the maximum point within a T-wave interval beginning 250 ms following the Q wave of the QRS complex and extending for 200 ms. These are merely exemplary values. At step 204, the onset of a cardiac ischemia is detected based upon detection of a significant shortening of QTmax. Routine experimentation may be performed to determine what constitutes "significant" insofar as changes in QTmax are concerned (and insofar as any other changes referred to herein as being significant are concerned.) In one example, a 10% or greater change in a given parameter is deemed to be significant. Note that QTmax values may be derived from either paced or sensed events but values derived from paced and sensed events should not be combined. In addition, QTmax varies with heart rate and so should be normalized based on heart rate. Bazettte's equation (i.e. $QTc=QT/(RR)^{1/2}$) may be used for normalizing QTmax (and for normalizing other parameters discussed herein) or from related equations, such as $QTp=656/(1+(\text{heartrate}/100))$. By way of implementation, a look-up table can be employed that provides values derived from the equations so that the device itself need not calculate the equations.

Additionally, or in the alternative, at step 204, the device calculates an "ischemic burden" based on QTmax, which is representative of the proportion of the time ischemia is detected. In one example, the ischemic burden is a numerical value representative of the extent to and/or the time during which QTmax is shorter than its running average. Steps 200-204 are preferably performed once every 30 seconds.

So long as no ischemia is detected, steps 200-204 are merely repeated. If ischemia is detected, however, the patient is warned of the ischemia by application of an internal perceptible "tickle" notification signal, at step 206. If the device is configured to generate warning signals for other conditions, such as hyperglycemia or hypoglycemia, the device preferably employs different notification signal frequencies for the different warnings so that the patient can properly distinguish between different warnings. In addition, warning signals may be transmitted using a short-range telemetry system to a handheld warning device using techniques described within the above-referenced patent application to Wang et al. The handheld warning device thereby provides confirmation of the warning to the patient, who may be otherwise uncertain as to the reason for the internally generated tickle warning signal. Additionally, if so equipped, the device may automatically control therapy in response to the ischemia. For example, if a drug pump is implanted within the patient, the pump may be controlled to deliver suitable anti-thrombolytic medications directly to the patient. Implantable devices for delivering anti-thrombolytic drugs are discussed in U.S. Pat. No. 5,960,797 to Kramer, et al. The device may also change pacing parameters in response to the detection of ischemia to, for example, deactivate overdrive pacing, which may exacerbate the ischemia. Other forms of elevated pacing may be discontinued as well, such as AF suppression therapy or activity-based rate responsive pacing. Various techniques for controlling delivery of therapy in response to ischemia are discussed U.S. Pat. No. 6,256,538 to Ekwall, listed above. See also U.S. Pat. No. 6,377,852 to Bornzin et al., which provides techniques for slowing the heart rate in response to ischemia. In addition, if the device is an ICD, then it may be controlled to immediately begin charging defibrillation capacitors in expectation of delivery of a defibrillation shock, which may be needed if the ischemia triggers VF.

Hence, FIG. 3 provides an overview of technique that seeks to detect the onset of cardiac ischemia based primarily on changes in QTmax. As will be explained below, additional parameters of the IEGM signal, such as ST deviation, may be employed to confirm the detection made based upon to QTmax. Insofar as the detection of T-waves at step 200 is concerned, the invention may exploit techniques set forth in U.S. Patent Application Serial Number 2004/0077962 of Kroll, published Apr. 22, 2004, entitled "System and Method for Monitoring Blood Glucose Levels Using an Implantable Medical Device." Certain techniques described therein are particularly well suited for detecting T-waves with a high degree of accuracy to permit precise detection of features of the T-wave (such as its peak) so as to achieve more precise measurement of QRS/T-wave intervals. The patent application to Kroll is fully incorporated by reference herein. The invention also may exploit T-wave detection techniques set forth within the aforementioned patent application to Min et al., which help prevent P-waves from being misinterpreted as T-waves on unipolar sensing channels.

Figure 4:
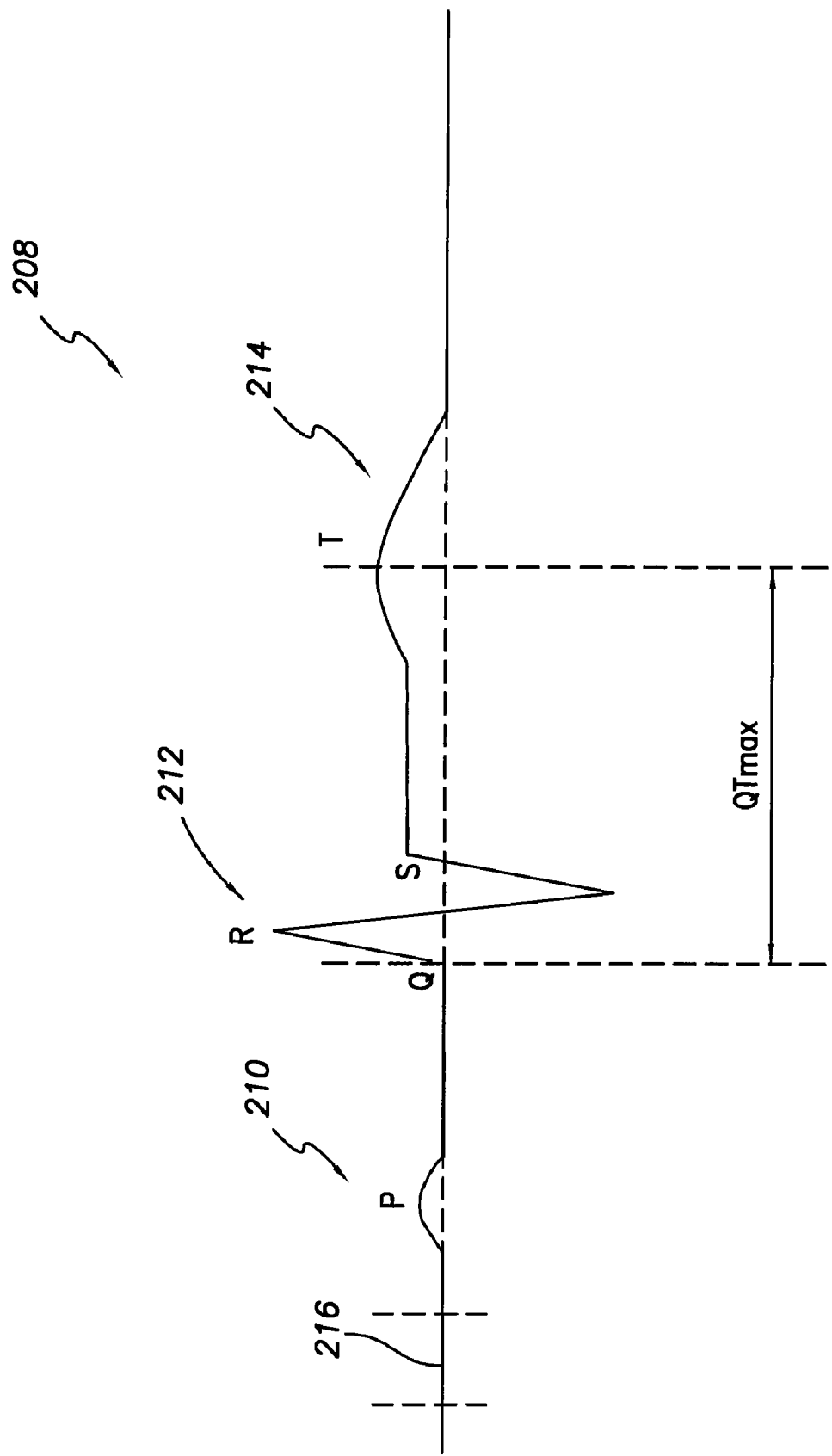
FIG. 4 is a graph providing a stylized representation of the IEGM of a single heartbeat, particularly illustrating the QTmax interval.

FIG. 4 illustrates the QTmax interval. Briefly, the figure provides a stylized representation of an exemplary IEGM trace 208 for a single heartbeat for a patient suffering myocardial ischemia. The stylized representation of the IEGM signal of FIG. 4 is provided for illustrative purposes and should not be construed as an actual, clinically detected IEGM signal. The heartbeat includes a P-wave 210 representative of an atrial depolarization, a QRS complex 212 representative of a ventricular depolarization and a T-wave 214 representative of ventricular repolarization. The QRS complex itself is defined by points Q, R, and S. Q represents the beginning of the complex; R represents the peak of the complex; and S represents the end of the complex. In the examples described and illustrated herein, the aforementioned QTmax interval is specified as the time interval from point Q to the peak or maximum amplitude point of T-wave. However, QTmax may alternatively be calculated based on other points or features of the QRS complex, such as the R point or the S point of the complex, so long as the calculations are consistent. As it is used herein, the "Q" of QTmax generally refers to the QRS complex and not specifically to the Q point of the QRS complex. Hence, the term QTmax encompasses RTmax as one example and STmax as another example. Also, in the particular example of FIG. 4, the peak of the T-wave is positive, i.e. it is greater than a baseline voltage of the IEGM signal. This need not be the case. In other examples, the peak has a negative value with respect to a baseline of the IEGM signal. The polarity of the entire signal may also be reversed. Herein, the peak or maximum amplitude of T-wave refers to the peak or maximum of the absolute value of the difference between the T-wave voltage and the baseline voltage of the IEGM signal. The baseline voltage 216 may be measured by taking an average of several voltage samples during an interval prior to the P-wave, as shown. The interval may be, for example, 50 milliseconds (ms) in duration, beginning 100 ms prior to the P-wave. Alternatively, and more preferably, the interval may be timed relative to the QRS complex. If timed relative to the QRS complex, the interval may commence, e.g., 80 ms prior to the R wave of the QRS complex, though, in many cases, the interval can be initiated earlier, such as 250 ms prior to the R wave Also alternatively, a single detection point may be used, rather than a detection interval.

Figure 5:
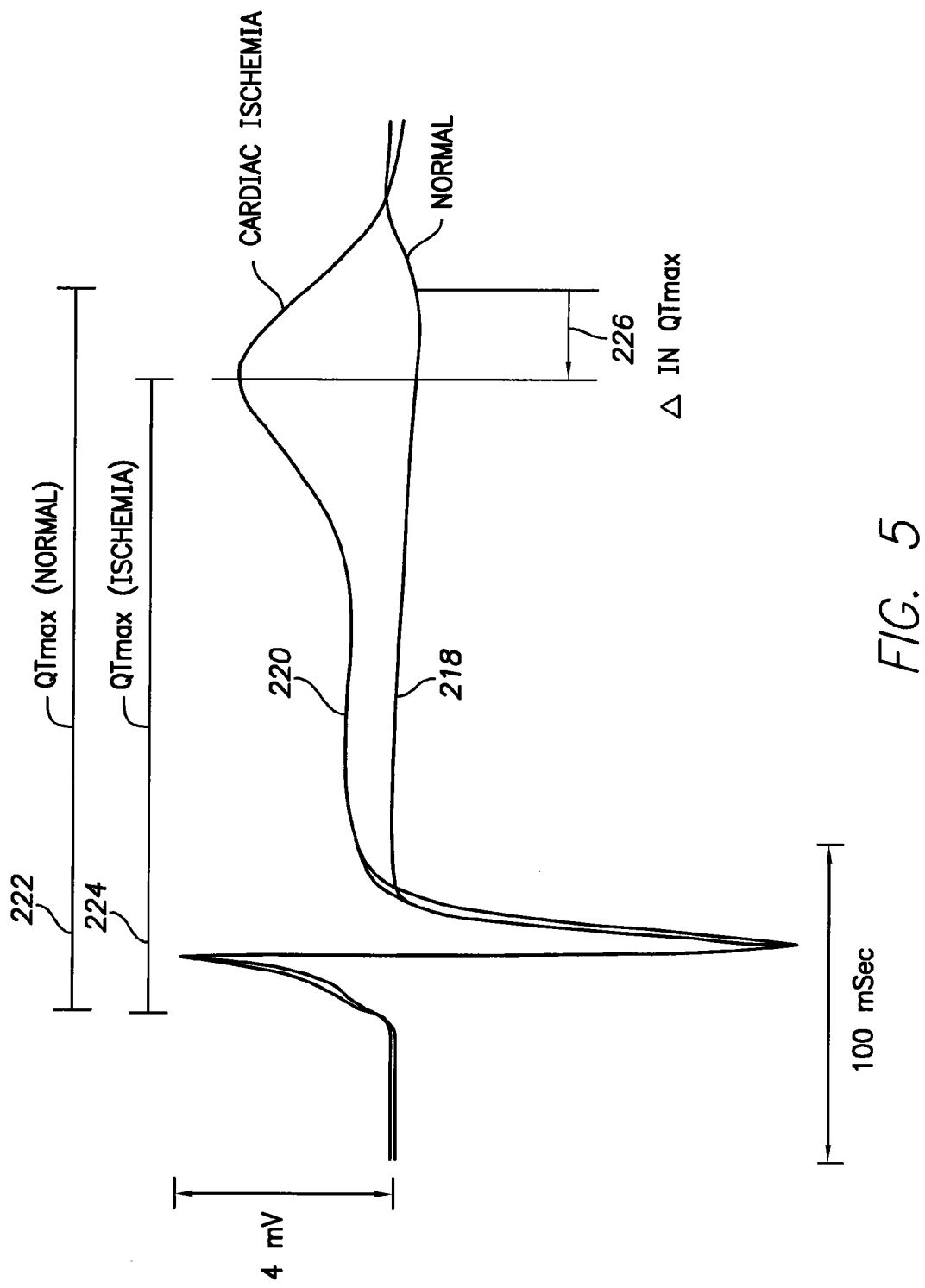
FIG. 5 is a graph providing exemplary representations of the IEGM of a single heart beat, particularly illustrating a reduction in the QTmax interval caused by cardiac ischemia.

FIG. 5 illustrates change in QTmax brought on by acute myocardial ischemia. A first exemplary IEGM trace 218 represents a heartbeat of a patient without cardiac ischemia, hypoglycemia or hyperglycemia. A second trace 220 illustrates the heartbeat for the patient suffering an acute myocardial ischemia. The traces are IEGM signals derived from voltage differences between the tip of a right ventricular (RV) lead and the device case. Note first that the IEGM trace for the healthy patient exhibits a T-wave that is reversed in polarity with respect to T-wave of the patient suffering the ischemia. T-wave inversion is typical during ischemia as well as during other conditions such as electrolyte abnormalities, which influence repolarization. Therefore, FIG. 5 illustrates that the QTmax feature is valid even in the presence of a T-wave inversion. In any case, for the purposes of ischemia detection, the peak of the T-wave during ischemia occurs earlier than the corresponding peak without ischemia. In other words, QTmax during ischemia 222 is shorter than QTmax without ischemia 224. Hence, a large positive value of ΔQTmax (226) is observed, where ΔQTmax represents the amount of the reduction in QTmax relative to some historical baseline. A negative value of ΔQTmax is associated with an increase in interval length. In the example FIG. 5, ΔQTmax is represented as a positive number. Note that significant negative ΔQTmax intervals may also be observed which, as will be explained below, are instead indicative of hypoglycemia.

ΔQTmax is the value used to detect the onset of ischemia. Preferably, any change in QTmax from a current baseline value is tracked. In one example, the device tracks a running average of QTmax intervals (derived from sensed events and normalized based on heart rate) for use as a baseline value. Different baseline values may be calculated for different heart rate ranges. In any case, for each new heartbeat, the device compares the QTmax interval for that heartbeat against the appropriate baseline to calculate ΔQTmax for that heartbeat. ΔQTmax values are averaged over, e.g., eight to sixteen heartbeats and then compared against a predetermined QTmax-based threshold. If the average exceeds the threshold, cardiac ischemia is thereby indicated. The threshold is a programmable value set, for example, based upon a percentage of the running average of the QTmax interval. In one specific example, if ΔQTmax is a positive value, which exceeds 10% of the running average of the QTmax intervals, cardiac ischemia is thereby indicated (i.e. QTmax has been found to be reduced by 10%). Otherwise conventional threshold comparison techniques may be employed for use with ΔQTmax. In another example, rather than comparing an average based on eight to sixteen values to the threshold, the occurrence of only a single ΔQTmax value exceeding the threshold is indicative of ischemia. In yet another example, if ΔQTmax exceeds the threshold for three out of five heartbeats, ischemia is indicated. Multiple thresholds may be defined, if desired, to trigger warning signals indicative of different levels of urgency. For example, if ΔQTmax exceeds a first, lower threshold, a warning signal indicative of a moderate ischemia is issued. If ΔQTmax exceeds a higher threshold, a second warning signal indicative of a more serious ischemia is issued. As can be appreciated, a wide variety of specific implementations may be provided in accordance with the general techniques described herein. Routine experimentation may be performed to determine appropriate threshold levels.

Hence, FIGS. 3-5 provide an overview of techniques for detecting the onset of cardiac ischemia based on changes in the QTmax interval. As will be explained below, particularly with reference to FIG. 13, ST deviation may be used to corroborate any cardiac ischemia detection made based upon QTmax intervals. Other parameters may be used as well to corroborate the detection of cardiac ischemia, including post T-wave-based detection parameters described in the above-referenced patent application to Wang et al. and T-wave energy-based parameters and T-wave slope-based parameters described in the above-referenced patent application Min et al.

Cardiac Ischemia Detection Based on ST Deviation and QTend

Figure 6:
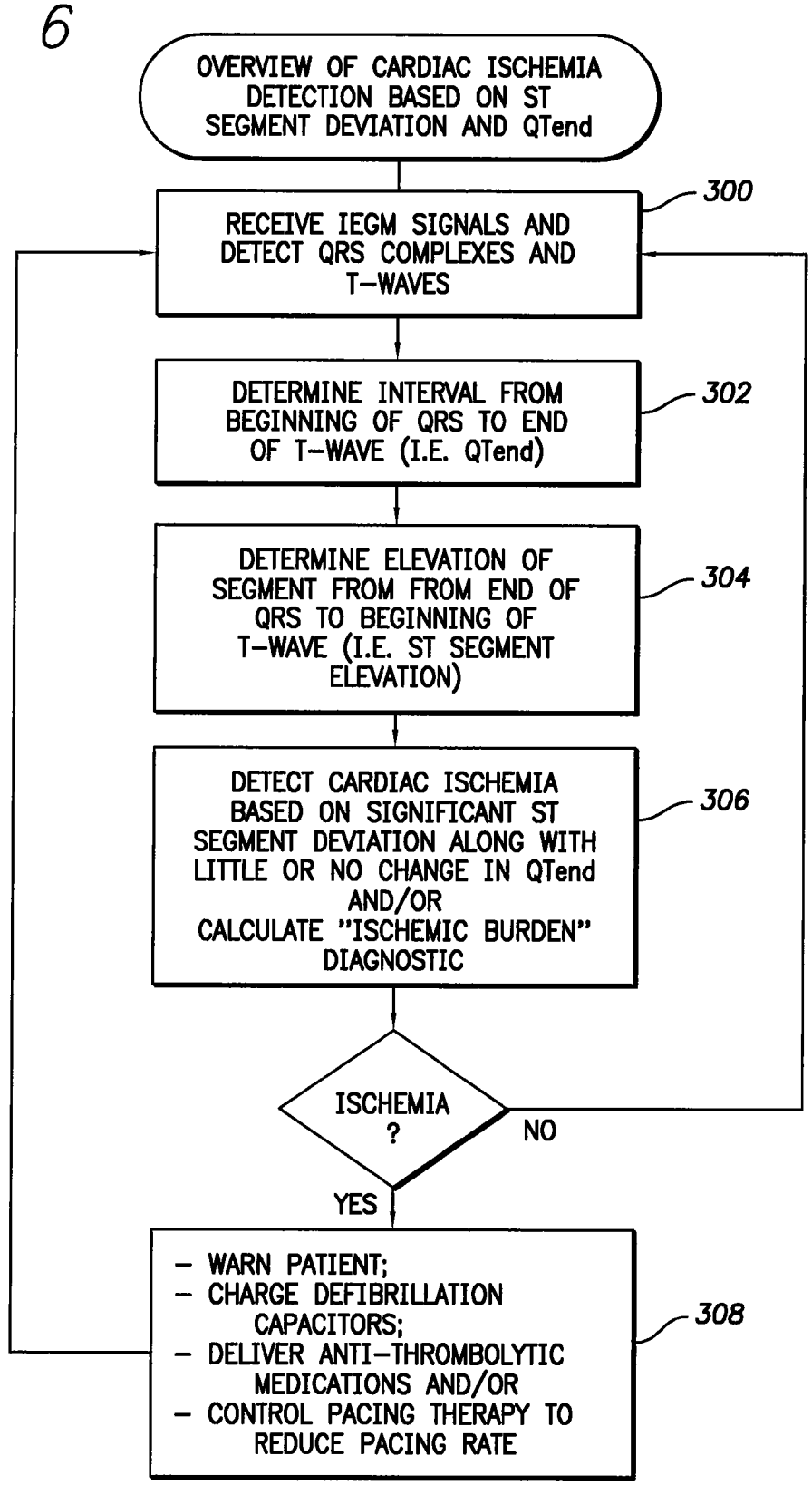
FIG. 6 is a flow chart providing an overview of an exemplary method performed by the device of FIG. 2 for detecting cardiac ischemia based primarily on a significant deviation in the ST segment along with little or no change in the QTend interval.

FIG. 6 provides an overview of a QTend-based cardiac ischemia detection technique performed by the device of FIG.

2. Many aspects of the technique are similar to those of the technique of FIG. 3 and will not be described again in detail. Initially, at step 300, IEGM signals are received and QRS-complexes and T-waves are identified therein. Then, the interval from the beginning of the QRS to the end of the T-wave is calculated, at step 302. This interval is referred to herein as QTend. In the examples described and illustrated herein, the QTend interval is specified as the time interval from point Q of the QRS complex to the end point of the T-wave. The end point of the T-wave may be defined as the first point in time at which, after the peak of the T-wave, the IEGM signal has returned for several consecutive samples (e.g. 3 samples at 512 Hz sample rate) to a value within a range of values close to the isoelectric baseline. This range may be based upon the IEGM value at the peak of the T-wave (e.g. baseline ±5% of the peak). Alternately, the end point of the T-wave may be defined as the point in time after the peak of the T-wave at which the derivative of the IEGM signal has returned for several samples to a value within a range of values close to zero. However, as with QTmax, QTend may alternatively be calculated based on other points or features of the QRS complex, such as the R point or the S point of the complex, so long as the calculations are consistent. The elevation of the interval from the end of the QRS complex to the beginning of the T-wave is also calculated, at step 304. This interval is referred to herein as the ST segment, its elevation is referred to as the ST elevation, and changes in the ST elevation is the ST deviation. Otherwise conventional techniques for detecting ST segment elevation may be used. Detection of ST segment elevation is discussed, for example, in U.S. Pat. Nos. 6,016,443 and 6,256,538 to Ekwall, listed above. At step 306, the onset of a cardiac ischemia is detected based upon observation of a significant deviation in the ST segment along with little or no change in QTend. A deviation in the ST is preferably calculated as a change in the average amplitude of the ST segment. Since the polarity of the IEGM signal is arbitrary, this may, in some cases, represent an increase in voltage of the ST segment and in other cases a decrease in voltage. It is the change in ST segment elevation that is important. As before, data from paced and sensed events should not be combined. QTend values should be normalized based on heart rate. Moreover, ST segments may be referenced beat-by-beat to either the PQ or TP regions of the IEGM.

Additionally, or in the alternative, at step 306, the device calculates an ischemic burden based on ST deviation and QTend, which is representative of the risk of ischemia. In one example, the ischemic burden is a single metric value derived from ST deviation and changes in QTend. Techniques for combining different parameters into a single metric value are set forth in published U.S. Patent Application 2004/0138716 to Koh et al., entitled "System and Method for Detecting Circadian States Using an Implantable Medical Device," published Jul. 15, 2004. If QTend and ST deviation are measured for diagnostic purposes only, steps 300-306 are preferably performed once an hour to calculate and record the ischemic burden. If measured for detecting ischemia, steps 300-306 are preferably performed more often, e.g. once every 30 seconds. In any case, so long as no ischemia is detected, steps 300-306 are merely repeated. If ischemia is detected however, the patient is warned of the ischemia at step 308, and, if so equipped, the device automatically controls therapy in response to the ischemia. If the device is an ICD, it may be controlled to immediately begin charging defibrillation capacitors.

Figure 7:
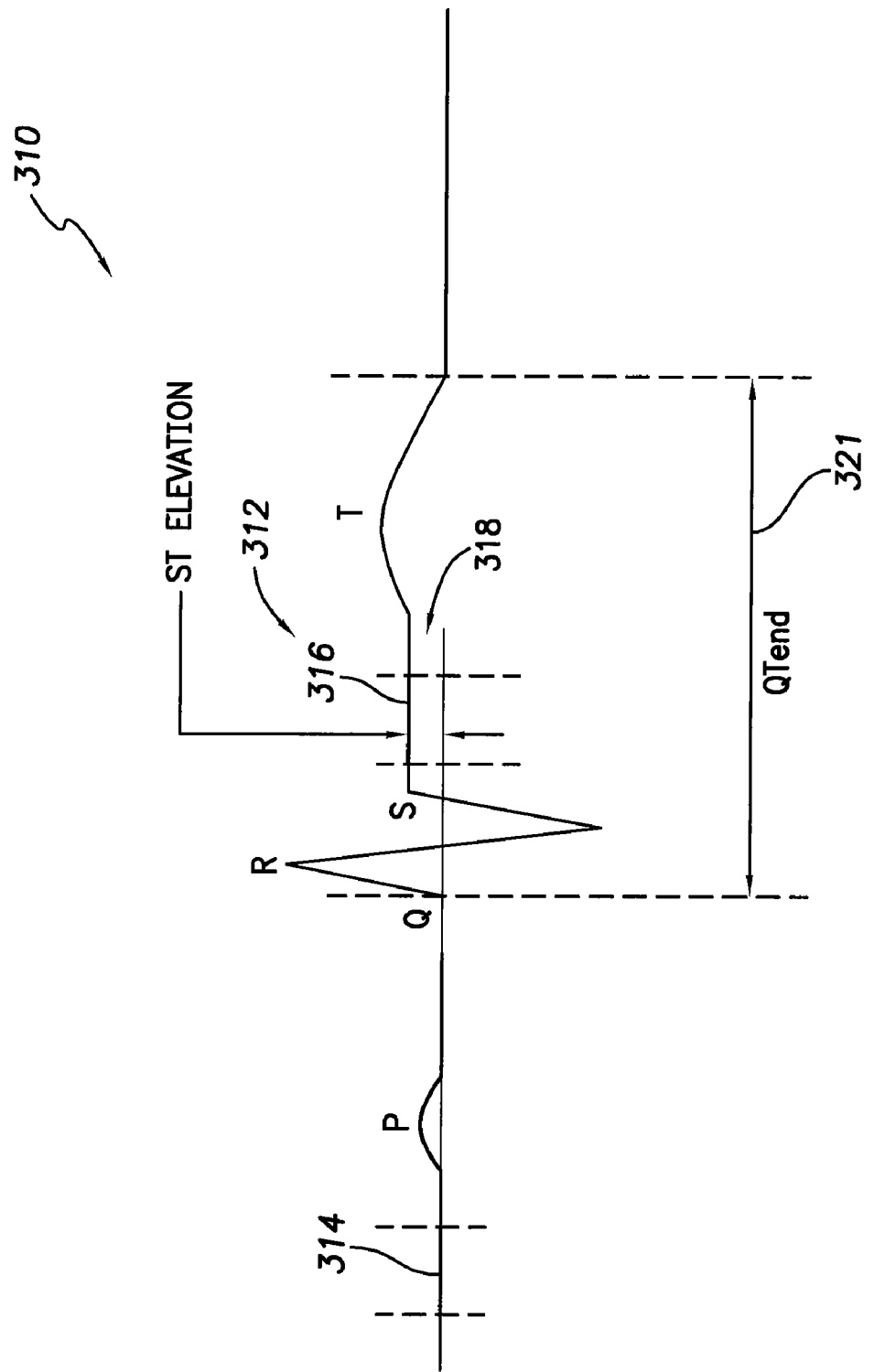
FIG. 7 is a graph providing a stylized representation of the IEGM of a single heartbeat, particularly illustrating ST deviation and the QTend interval.

Hence, FIG. 6 provides an overview of technique that seeks to detect the onset of cardiac ischemia based on a combination of ST deviation and QTend. Additional parameters of the IEGM signal, such as the aforementioned QTmax interval, may be employed to confirm the detection. FIG. 7 illustrates ST segment elevation and the QTend interval. Briefly, FIG. 7 provides a stylized representation of an exemplary IEGM trace 310 for a single heartbeat for a patient suffering a myocardial ischemia. The ST segment 312 is the interval from the end of the QRS complex to the start of the T-wave. The duration of this interval is not of interest in this technique. However, its deviation, i.e. the extent to which its elevation changes over time is of interest. To calculate the elevation of an individual ST segment, the device identifies a window 316 with the ST segment. The elevation of the ST segment (relative to a baseline voltage) within the window is denoted by reference numeral 318. The ST segment elevation may be measured during a specified interval following the QRS complex, as shown. The interval may be, for example, 50 ms in duration, beginning 50 ms following the R wave of the QRS complex. For ventricular paced events, the interval may begin, for example, 80 ms following a V-pulse and extend for 50 ms. These are merely exemplary values. The elevation may be quantified based on the mean of the ST segment sample. Meanwhile, the QTend interval is the time interval between the beginning of the QRS complex and the end point of the T-wave, i.e. the point at which the slope of the T-wave following its peak becomes substantially flat. Techniques for detecting T-wave slope are set forth in the aforementioned patent application to Min et al. The QTend interval is denoted by reference numeral 321.

Figure 8:
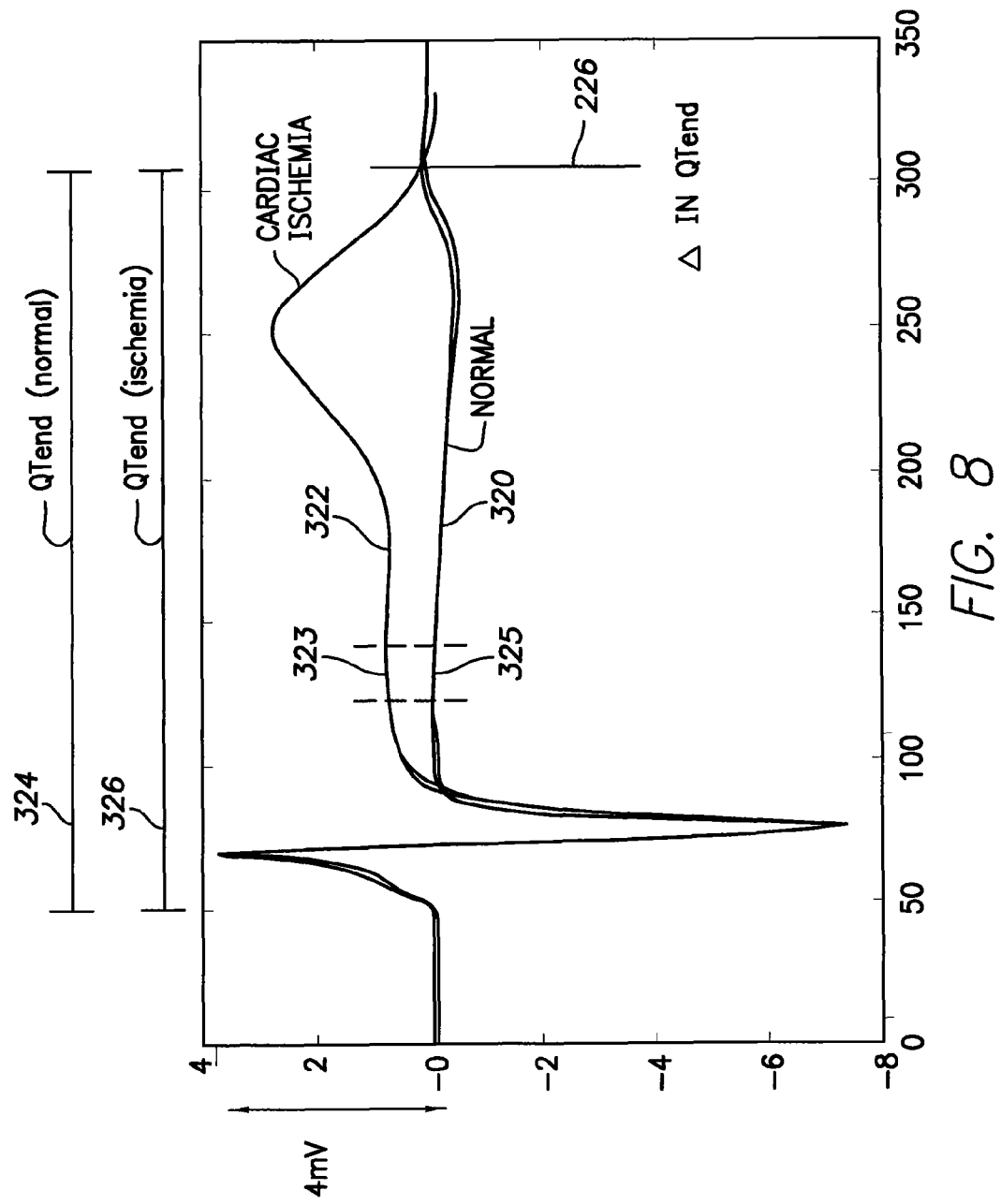
FIG. 8 is a graph providing exemplary representations of the IEGM of a single heart beat, particularly illustrating a significant deviation in the ST segment caused by cardiac ischemia, along with a lack of change in QTend.

FIG. 8 illustrates changes in ST segment elevation brought on by acute myocardial ischemia. A first exemplary IEGM trace 320 represents a heartbeat of a healthy patient, i.e. one not subject to cardiac ischemia or hypo/hyperglycemia. A second trace 322 illustrates the heartbeat for a patient suffering an acute myocardial ischemia. As with other traces illustrated herein, the IEGM signals of FIG. 8 are exemplary representations of IEGM signals provided for illustrative purposes only. Comparing the two traces, the elevation of the ST-segment during ischemia (323) is much greater than the elevation of the ST-segment without ischemia (325), i.e. there is a significant ST deviation. However, there is little or no change in QTend, i.e. the absolute value of ΔQTend is substantially zero, where ΔQTend represents the amount of the reduction (relative to some historical baseline), if any, in QTend interval duration. (A positive value of ΔQTmax is associated with a decrease in interval length. A negative value of ΔQTmax is associated with an increase in interval length. For the purposes of the technique of FIG. 6, only the magnitude of any change in QTend is important.) Hence, QTend helps corroborate the detection of ischemia made based on ST deviation. In particular, as will be explained in more detail below with reference to FIGS. 9-10, a change in ST segment elevation brought on by hypoglycemia will additionally trigger a significant increase in QTend. Hence, without an examination of QTend, it may not be possible to reliably distinguish a change in ST segment elevation caused by ischemia from a change caused by hypoglycemia.

Preferably, any changes in the ST segment elevation and in QTend from current baseline values are tracked. In one example, the device tracks a running average of the ST segment elevation (as derived from sensed events) and then, for each new heartbeat, the device compares the ST segment elevation for that heartbeat against the running average to calculate a ST deviation value for that heartbeat. Note that, typically, ST segment values need not be normalized based on heart rate though, in some cases, it may be advantageous to normalize. The device also tracks a running average of the QTend interval (as derived from sensed events and normalized based on heart rate) and then, for each new heartbeat, compares the QTend interval for that heartbeat against the running average to calculate a ΔQTend value for that heartbeat. The value of ST deviation for the heartbeat is averaged over, e.g., eight to sixteen heartbeats and compared against a predetermined deviation-based threshold. If the average exceeds the threshold, then the absolute value of ΔQTend is also averaged over eight to sixteen heartbeats and compared against a predetermined ΔQTend-based threshold. If ST deviation exceeds its respective threshold (indicating a significant change in ST segment elevation), but the absolute value of ΔQTend does not exceed its respective threshold (indicating little or no change in QTend), then cardiac ischemia is thereby indicated. (If ST deviation exceeds its respective threshold and either QTend or QTmax, or preferably both, are lengthened significantly, an indication of hypoglycemia may instead be provided. See FIG. 13, discussed below.) Alternatively, the ST segment elevation may be directly compared against an elevation-based threshold. In this regard, any of a variety of threshold-based techniques may be exploited wherein, e.g., values are compared against historical baseline values, absolute values, etc.

The various thresholds are programmable values set, for example, based upon respective running averages. In one specific example, the threshold for ΔQTend is set to 10% of the running average of the QTend intervals. The threshold for ST deviation may be set, for example, based on some percentage (e.g. 20%) of a running average of peak-to-peak voltage swings in QRS complexes, i.e. based on a percentage of the average difference from a maximum positive voltage to a maximum negative voltage within each QRS complex. Alternatively, the threshold for ST deviation may be set to a preset voltage difference, such as 0.25-0.5 milli-Volts (mV). As with the QTmax-based technique, alternative threshold comparison techniques may instead be used. Multiple thresholds may be defined, in some implementations, to trigger warning signals indicative of different levels of urgency. Routine experimentation may be performed to determine appropriate threshold levels.

Hence, FIGS. 6-8 provide an overview of techniques for detecting the onset of cardiac ischemia based on an examination of ST segment deviation in conjunction with QTend interval. Other parameters may be used to further corroborate the detection of cardiac ischemia, such as the QTmax interval and parameters described in the above-referenced patent applications to Wang et al. and Min et al. In the next section, techniques for detecting hypoglycemia will be described.

Hypoglycemia Detection Based on QTmax and/or QTend

Figure 9:
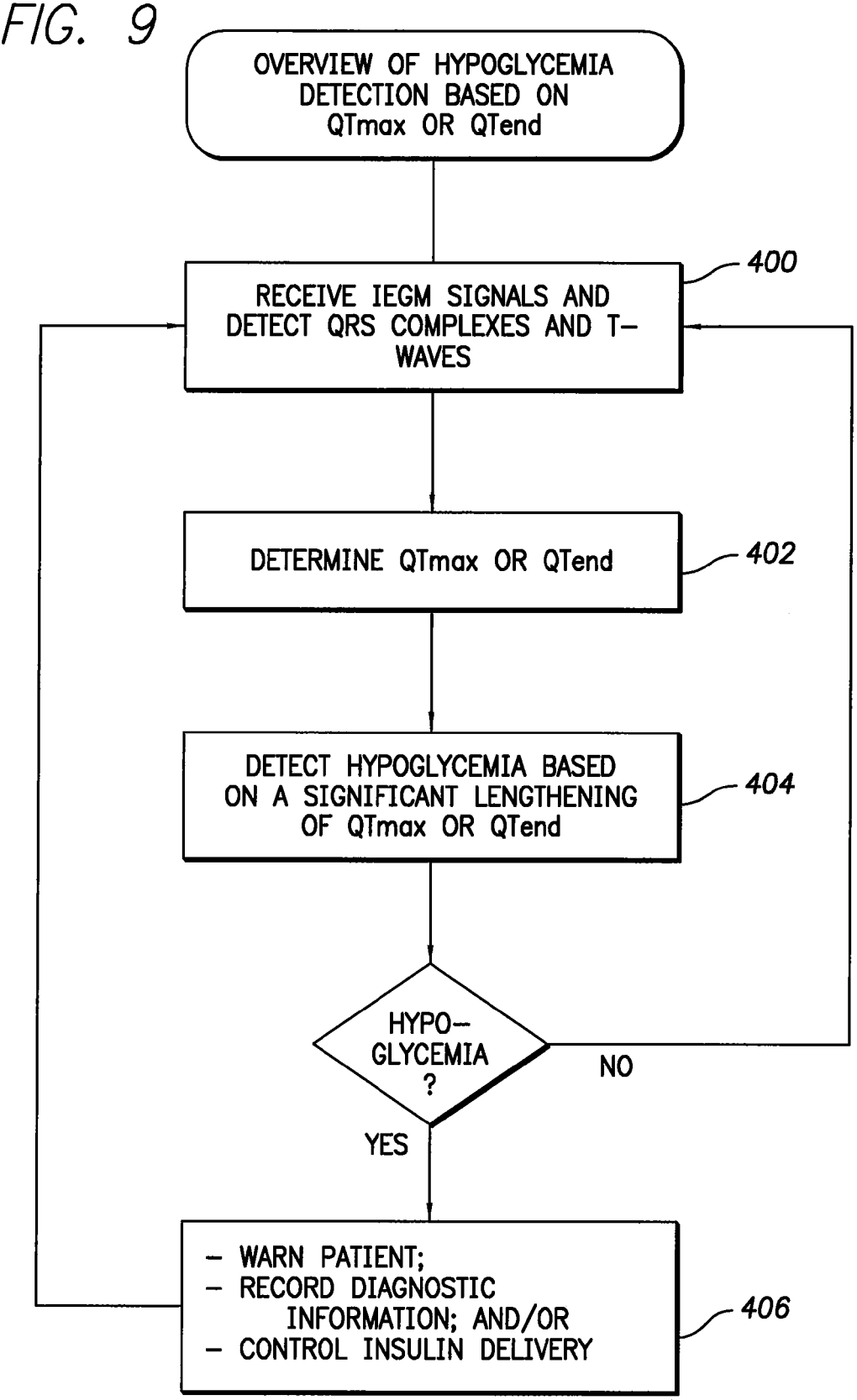
FIG. 9 is a flow chart providing an overview of an exemplary method performed by a hypoglycemia detection system of FIG. 2 for detecting hypoglycemia based primarily on a significant lengthening of either QTmax or QTend.

FIG. 9 provides an overview of hypoglycemia detection techniques performed by the device of FIG. 2. Many aspects of this technique are similar to those of the ischemia detection techniques described above and will not be described again in detail. Initially, at step 400, IEGM signals are received and QRS-complexes and T-waves are identified therein. Then, at step 402, QTmax and QTend intervals are measured. At step 404, the onset of hypoglycemia is detected based upon observation of a significant lengthening of either QTend or QTmax or both. In this regard, both QTmax and QTend increase due to hypoglycemia. Hence, one or the other is sufficient to detect hypoglycemia. Both are preferred to enhance detection reliability. A change in ST segment elevation may be used to further corroborate the detection (see FIG. 13). As before, data from paced or sensed events should not be combined. QTmax and QTend intervals should be normalized based on heart rate.

Additionally, or in the alternative, ST deviation, QTmax and QTend may be stored for diagnostic purposes. The device may calculate a single value representative of the risk of hypoglycemia based on a combination of ST deviation, QTmax and QTend, similar to the ischemic burden discussed above. In any case, so long as hypoglycemia is not detected, steps 400-404 are merely repeated. If hypoglycemia is detected, however, the patient is warned, at step 406. Preferably, the warning signal differs from the one generated for ischemia. If so equipped, the device may automatically initiate therapy appropriate for responding to hypoglycemia. For example, if an insulin pump is implanted within a diabetic patient, the pump may be controlled to adjust the dosage of insulin in response to hypoglycemia. Techniques for controlling delivery of therapy in response to hypoglycemia are set forth in the Patent Application of Kroll, incorporated by reference above. Information regarding implantable insulin pumps may be found in U.S. Pat. No. 4,731,051 to Fischell and in U.S. Pat. No. 4,947,845 to Davis.

Figure 10:
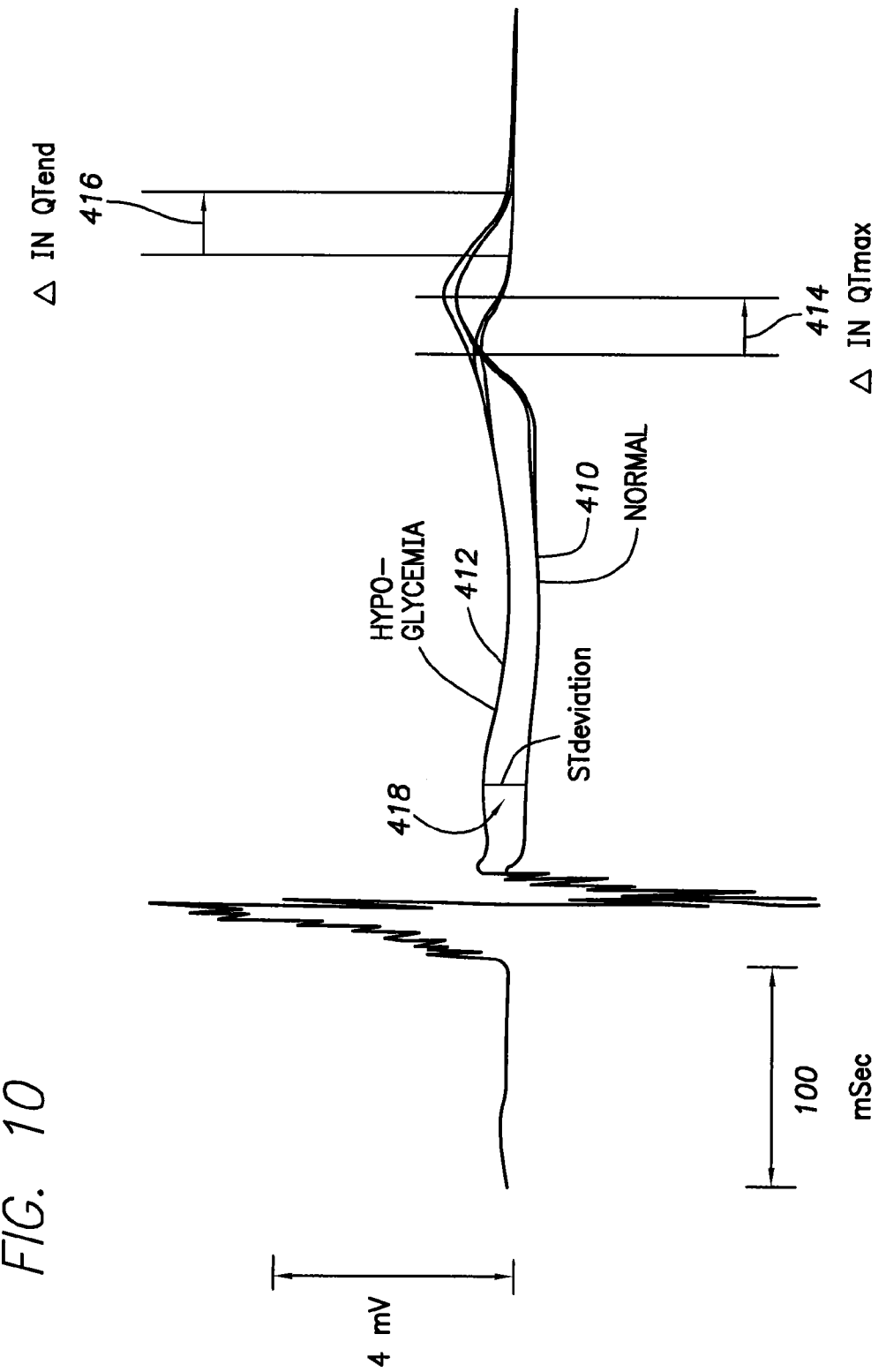
FIG. 10 is a graph providing exemplary representations of the IEGM of a single heartbeat, particularly illustrating a significant lengthening of both QTmax and QTend.

Hence, FIG. 9 provides an overview of technique that seeks to detect the onset of hypoglycemia based on a lengthening of QTmax or QTend. FIG. 10 illustrates QTmax and QTend brought on by hypoglycemia, as well as changes in ST segment deviation. A first exemplary IEGM trace 410 represents a heartbeat of a healthy patient, i.e. one not subject to hypo/hyperglycemia or cardiac ischemia. A second trace 412 illustrates the heartbeat for a patient suffering from hypoglycemia. As with other traces illustrated herein, the IEGM signals of FIG. 10 are exemplary representations of IEGM signals provided for illustrative purposes only. Comparing the two traces, there is a significant lengthening of both QTmax and QTend, i.e. both ΔQTmax and ΔQTend are large in magnitude. (As explained above, ΔQTmax and ΔQTend are defined as positive numbers for a reduction in interval length and as negative numbers for an increase in interval length.)

Hence, an increase in either QTmax or QTend or both allows the device to detect hypoglycemia. ST deviation may be used to corroborate the determination. As can be seen from FIG. 10, the elevation of the ST segment 410, 412 changes in response to hypoglycemia, yielding an ST segment deviation 418. Preferably, any changes in QTmax and/or QTend are measured with respect to baseline values of those parameters. In one example, the device tracks running averages QTmax and QTend (as derived from sensed events and normalized based on heart rate) for use as baseline values. Different baseline values may be calculated for different heart rate ranges. Then for each new heartbeat, the device compares new values for those parameters against the appropriate baseline values to calculate ΔQTmax 414 and ΔQTend 416 values for that heartbeat. In the example, the ΔQTmax and ΔQTend values are averaged over eight to sixteen heartbeats. ΔQTmax is compared against a predetermined ΔQTmax-based threshold and ΔQTend is compared against a predetermined ΔQTend-based threshold and. These thresholds may differ in value from the corresponding thresholds discussed above. If ΔQTmax and ΔQTend both exceed their respective thresholds, an indication of hypoglycemia is thereby provided. The various thresholds are programmable values set, for example, based upon percentages of running averages of the respective interval. Again, multiple thresholds may be defined, if desired, to trigger warning signals indicative of different levels of urgency. Routine experimentation may be performed to determine appropriate threshold levels. In the next section, techniques for instead detecting hyperglycemia will be described.

Hyperglycemia Detection Based on ST Deviation, QTmax and QTend

Figure 11:
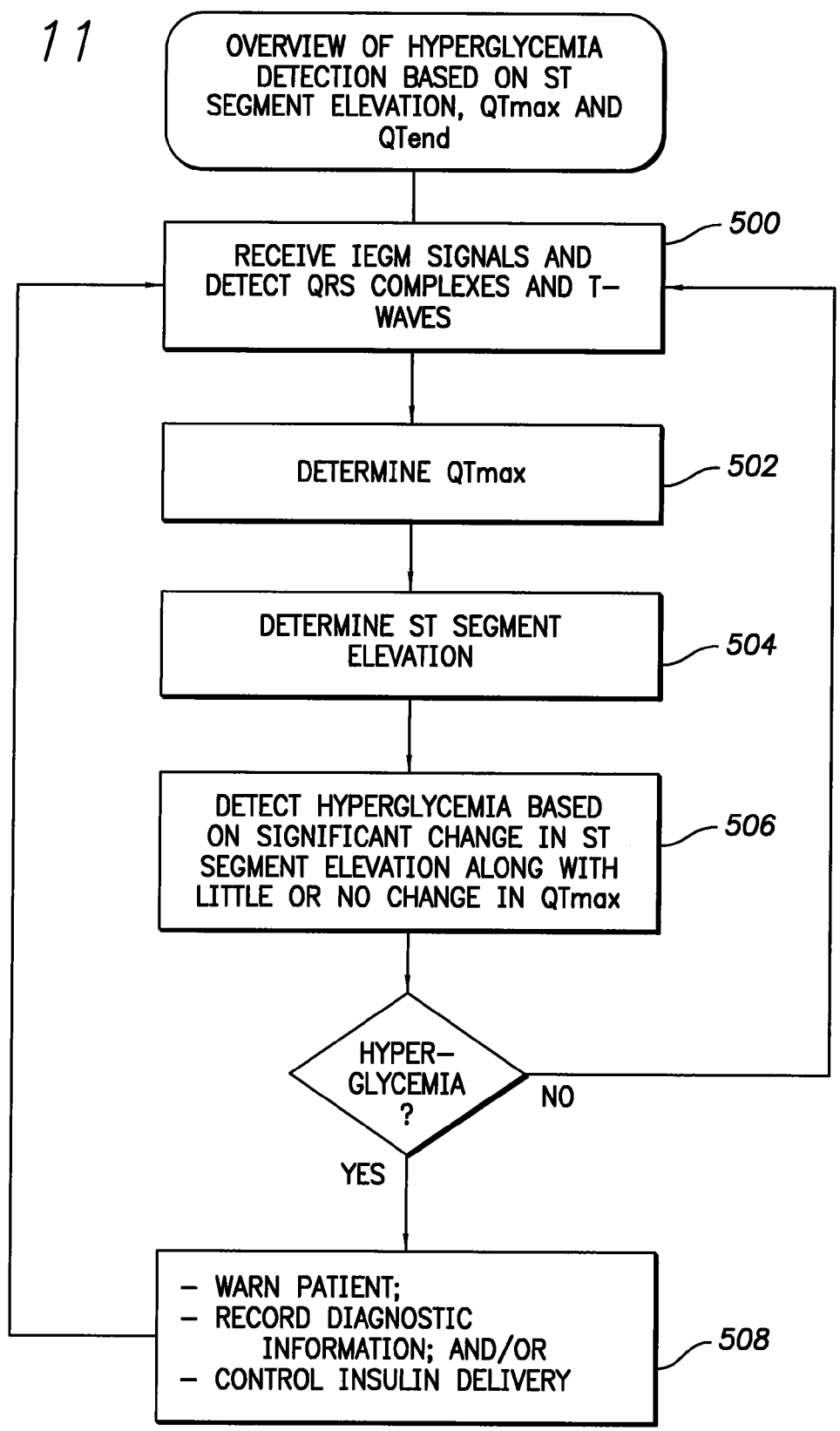
FIG. 11 is a flow chart providing an overview of an exemplary method performed by a hyperglycemia detection system of FIG. 2 for detecting hyperglycemia based primarily on a significant deviation in the ST segment along with little or no change in QTmax.

FIG. 11 provides an overview of hyperglycemia detection techniques performed by the device of FIG. 2. Many aspects of this technique are similar to those of the detection techniques described above and will not be described again in detail. Initially, at step 500, IEGM signals are received and QRS-complexes and T-waves are identified therein. Then, at step 502, QTmax intervals are measured and, at step 504, ST segment elevation is detected. At step 506, the onset of a hyperglycemia is detected based upon detection of a significant change in ST segment elevation along with little or no change in QTmax. A change in ST segment elevation along with a shortening of QTmax is instead indicative of cardiac ischemia. Note that, with hyperglycemia, neither QTmax nor QTend changes significantly. However, a change in ST segment elevation along with little or no change in QTend may also be indicative of either hyperglycemia or cardiac ischemia. So QTmax is observed instead of QTend. As before, data from paced and sensed events should not be combined. QTmax and QTend intervals should be normalized based on heart rate.

Additionally, or in the alternative, values representative of ST deviation, QTmax and QTend may be stored for diagnostic purposes. The device may calculate a single value representative of the risk of hyperglycemia based on a combination of ST deviation, QTmax and QTend, similar to the ischemic burden discussed above. In any case, so long as hyperglycemia is not detected, steps 500-506 are merely repeated. If hyperglycemia is detected, however, the patient is warned, at step 508, and, if properly equipped, the device automatically controls therapy appropriate for responding to hyperglycemia. If an insulin pump is implanted, the pump may be controlled to adjust the dosage of insulin in response to hyperglycemia. Techniques set forth in the patent application of Kroll, listed above, may be suitable for this purpose.

Figure 12:
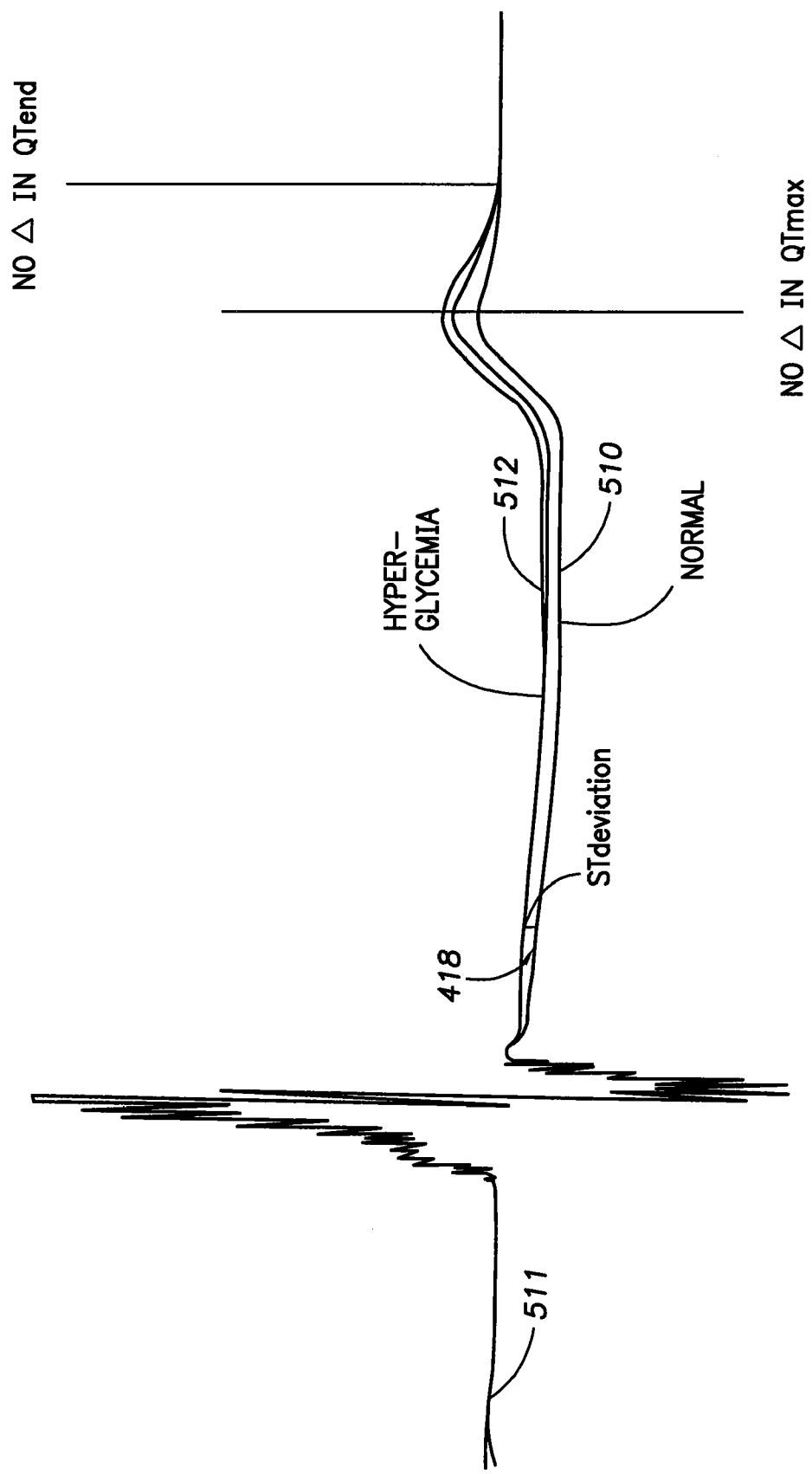
FIG. 12 is a graph providing exemplary representations of the IEGM of a single heart beat, particularly illustrating a significant deviation in ST segment caused by hyperglycemia, along with little or no change in QTmax.

Hence, FIG. 11 provides an overview of a technique that seeks to detect the onset of hyperglycemia based on a combination of ST deviation and QTmax. FIG. 12 illustrates changes in ST segment elevation brought on by hyperglycemia. A first exemplary IEGM trace 510 represents a heartbeat of a healthy patient, i.e. one not subject to hypo/hyperglycemia or cardiac ischemia. A second trace 512 illustrates the heartbeat for a patient with hyperglycemia. As with other traces illustrated herein, the IEGM signals of FIG. 12 are exemplary representations of IEGM signals provided for illustrative purposes only. Comparing the two traces, the elevation of the ST-segment changes, yielding an ST segment deviation 418. However, there is little or no change in QTmax, i.e. an absolute value of ΔQTmax is near zero. (There is also little or no change in QTend during hyperglycemia, i.e. an absolute value of ΔQTend is also near zero.)

Hence, an examination of QTmax allows the device to properly distinguish a change in ST segment elevation due to hyperglycemia from a change due to hypoglycemia or cardiac ischemia. Compare FIG. 12 with FIGS. 5, 8 and 10, described above. Preferably, any changes in ST segment elevation (as derived from sensed events) and QTmax (as derived from sensed events and normalized based on heart rate) are measured with respect to baseline values of those parameters and values for ST deviation and ΔQTmax are calculated for each heartbeat and averaged over multiple heartbeats. The averaged values are compared against respective thresholds. A warning of hyperglycemia is issued only if ST deviation exceeds its threshold whereas ΔQTmax remains below its thresholds. These thresholds may differ in value from corresponding thresholds discussed above. The various thresholds are programmable values set, for example, based upon respective running averages. Again, multiple thresholds may be defined, in some implementations, to trigger warning signals indicative of different levels of urgency. Routine experimentation may be performed to determine appropriate threshold levels.

What have been described thus far are various techniques for detecting cardiac ischemia, hypoglycemia or hyperglycemia based on various combinations of QTmax, QTend and ST deviation. Preferably, the device is configured to detect any of these conditions and to distinguish therebetween. This is discussed in the following section.

Combined Hypo/Hyperglycemia and Ischemia Detection Examples

Figure 13:
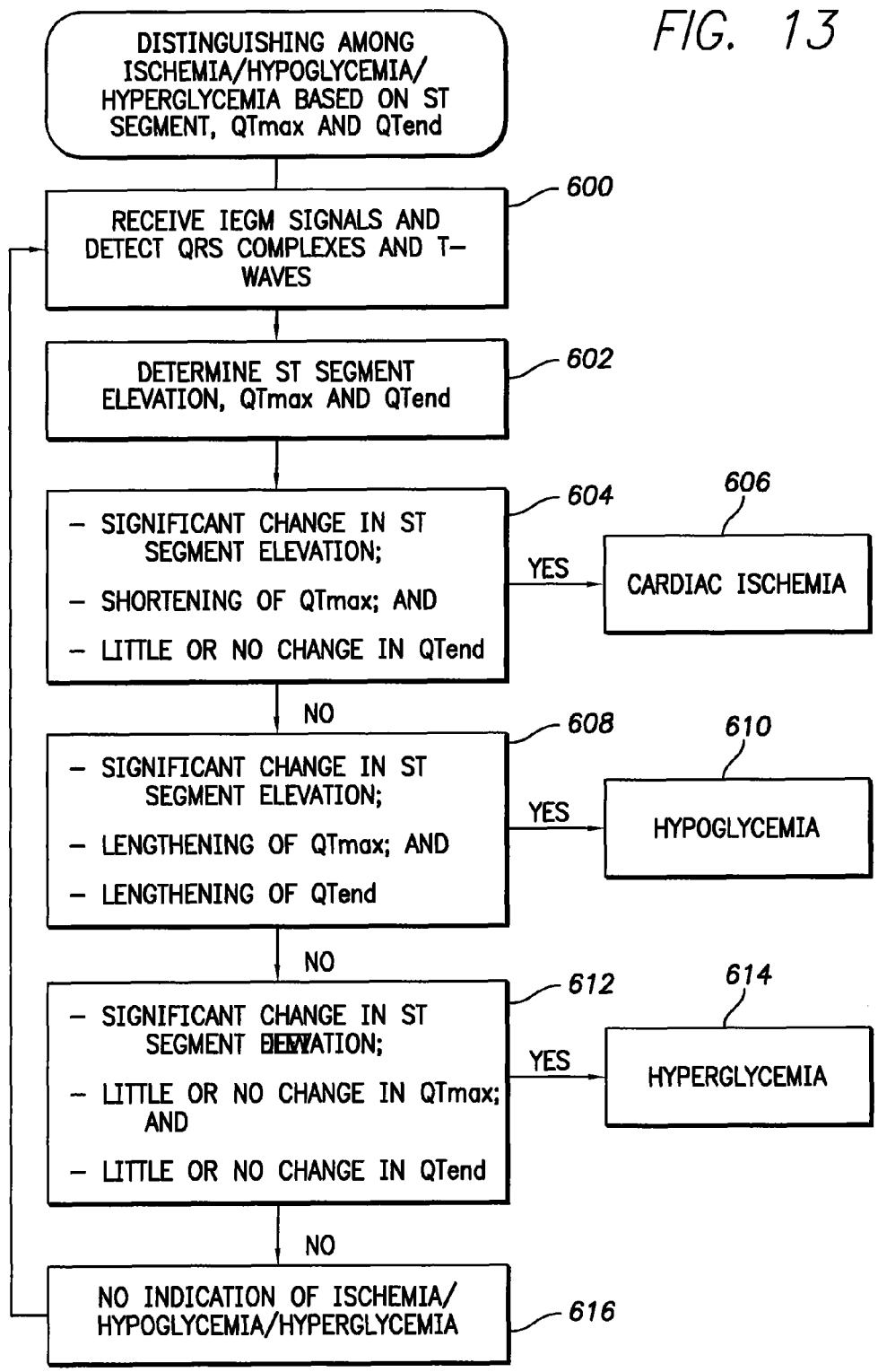
FIG. 13 is a flow chart providing an overview of an exemplary method performed by the implantable device of FIG. 2 for distinguishing among cardiac ischemia, hypoglycemia and hyperglycemia based on ST segment, QTmax, and QTend.

FIG. 13 illustrates an exemplary technique for distinguishing among cardiac ischemia, hypoglycemia and hyperglycemia wherein QTmax, QTend and ST deviation are each examined. Beginning at step 600, the implanted device receives IEGM signals and detect QRS complexes and T-waves. At step 602, the device determines ST segment elevation, QTmax and QTend for each individual heartbeat (as derived from either sensed events only or paced events only and properly normalized based on heart rate). Based upon these values, the device detects and distinguishes between cardiac ischemia, hypoglycemia and hyperglycemia. Briefly, at steps 604-606, the device detects cardiac ischemia based upon any significant change in ST segment elevation (i.e. a significant value for ST deviation) combined with a concurrent shortening of QTmax, so long as there is also little or no change in QTend. At step 608-610, the device detects hypoglycemia based upon any significant change in ST segment elevation combined with a lengthening of both QTmax and QTend. At steps 612-614, the device detects hyperglycemia based upon a significant change in ST segment elevation so long as there is little or no change in either QTmax or QTend. Appropriate warning signals are issued upon detection of ischemia, hypoglycemia or hyperglycemia. The above-described threshold-based techniques may be employed to make these various determinations. Note that the conditions set forth in the steps 604, 608 and 612 are listed above in Table I.

If none of the conditions set forth in steps 604, 608 and 612 are met, then no indication of ischemia, hypoglycemia or hyperglycemia is made, step 616, and processing instead returns to step 604 for examination of additional IEGM signals. In other words, no warning of ischemia, hypoglycemia or hyperglycemia is triggered unless each of the three parameters (ST deviation, QTmax and QTend) corroborates the diagnosis. This differs from the individual examples discussed above wherein an indication of ischemia, hypoglycemia or hyperglycemia may be made based upon significant changes in only one or two of the parameters. By examining all three parameters, a greater degree of reliability and specificity is achieved. Additional detection parameters may be examined as well, including otherwise conventional detection parameters or the parameters set forth in the aforementioned patent applications to Wang et al. and Min et al. IN any case, once the analysis is complete appropriate warnings are issued and therapy is adjusted.

Figure 14:
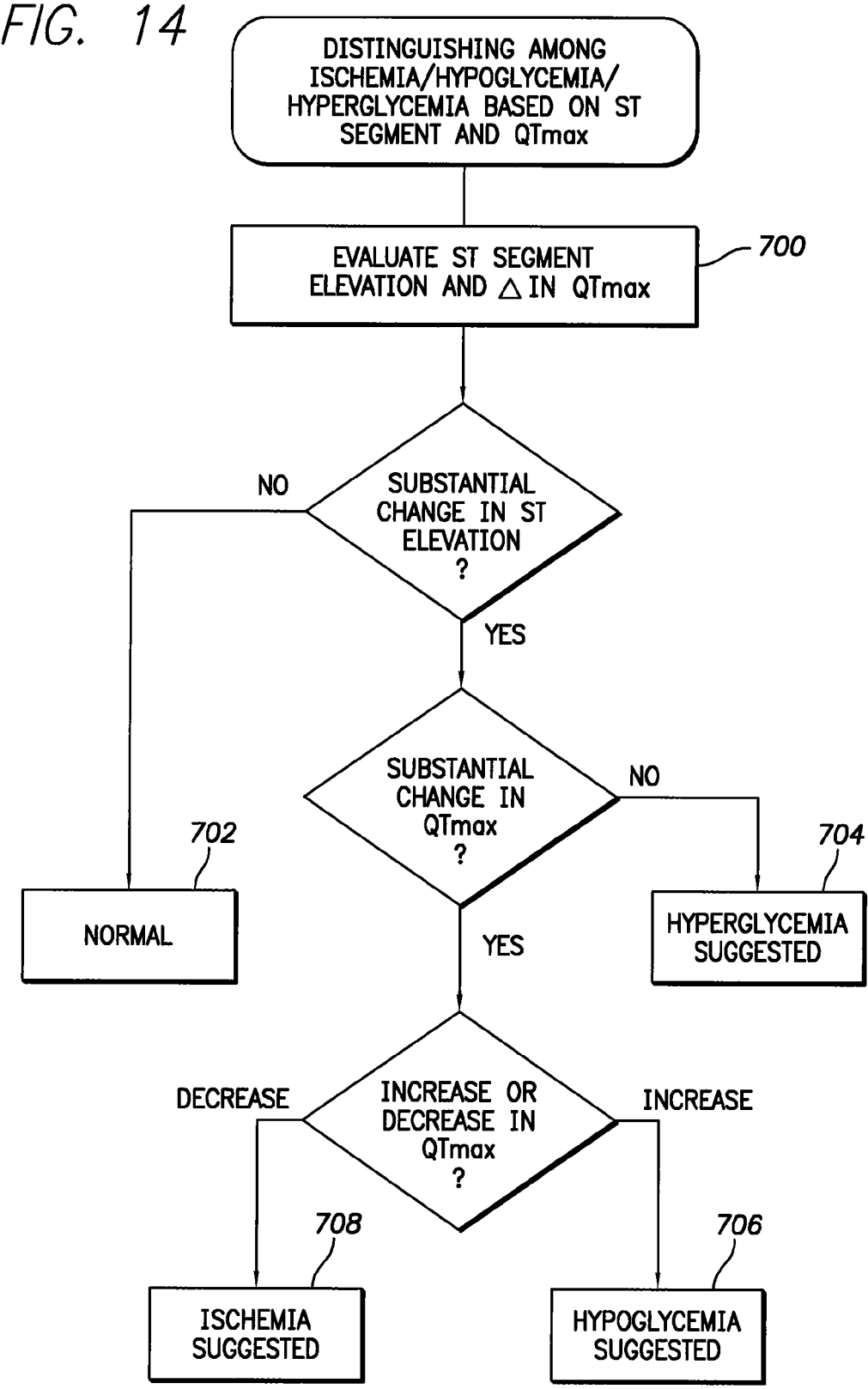
FIG. 14 is a flow chart providing an overview of an exemplary method performed by the implantable device of FIG. 2 for distinguishing among cardiac ischemia, hypoglycemia and hyperglycemia based on ST segment deviation and QTmax.

FIG. 14 illustrates an exemplary technique for distinguishing among cardiac ischemia, hypoglycemia and hyperglycemia based on just QTmax and ST segment elevation. Beginning at step 700, the implanted device evaluates ST segment elevation and ΔQTmax. If there is no substantial change in ST elevation, i.e. ST deviation is small, then the patient's condition is deemed to be normal, at step 702. However, if there has been a substantial change in ST elevation, then the device proceeds to determine whether there has also been a substantial change in QTmax, i.e. whether ΔQTmax exceeds a threshold representative of a significant change. If not, then hyperglycemia is suggested, at step 704. If ΔQTmax exceeds the threshold, however, the device determines whether QTmax has lengthened or shortened. If QTmax has lengthened, then hypoglycemia is suggested that step 706. If QTmax has become shorter, then ischemia is suggested that step 708. The above-described threshold-based techniques may be employed to make these various determinations. Appropriate warning signals are issued and therapy is adjusted.

Figure 15:
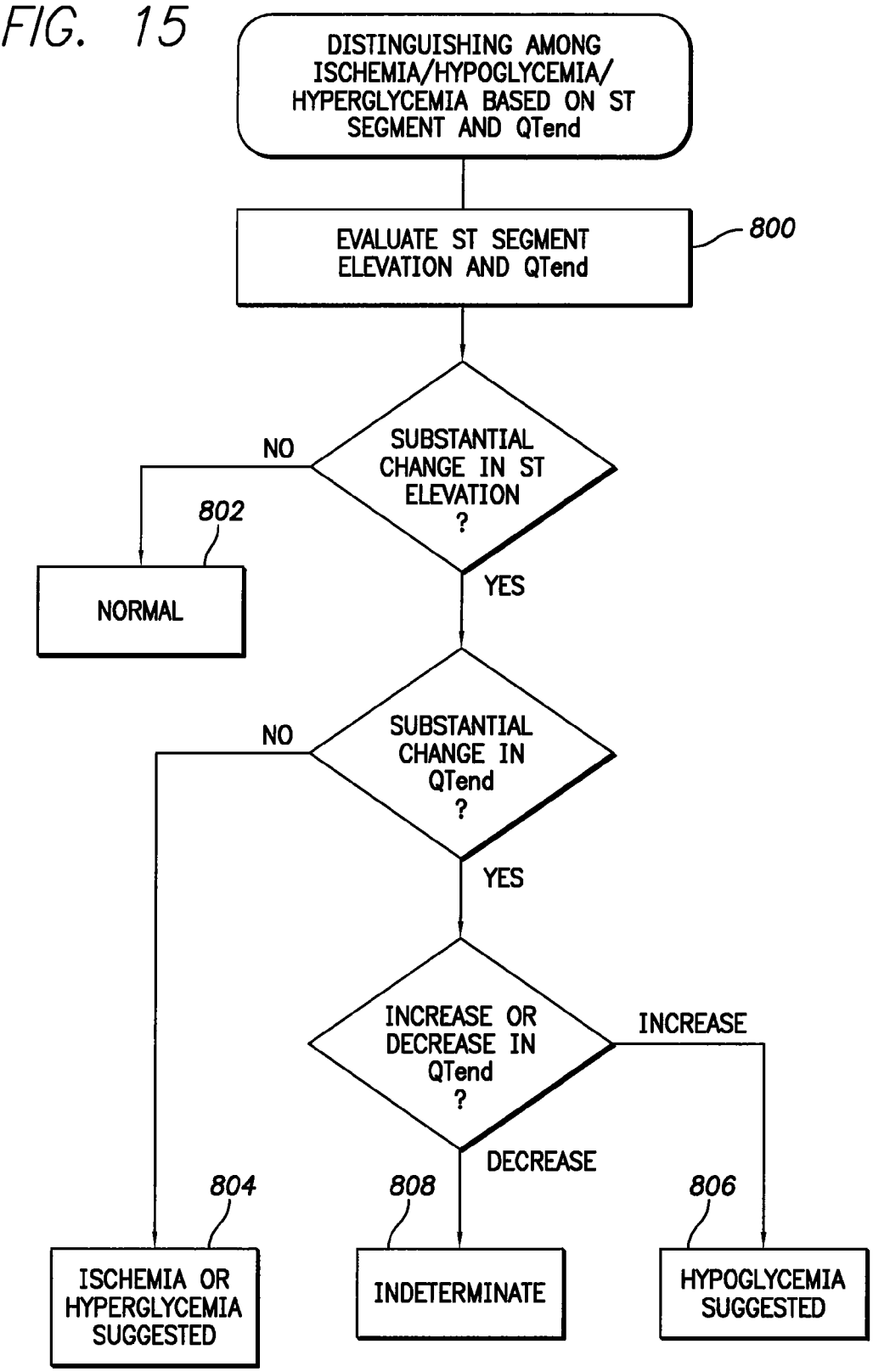
FIG. 15 is a flow chart providing an overview of an exemplary method performed by the implantable device of FIG. 2 for distinguishing among cardiac ischemia, hypoglycemia and hyperglycemia based on ST segment deviation and QTend.

FIG. 15 illustrates an exemplary technique for distinguishing among cardiac ischemia, hypoglycemia and hyperglycemia based on just QTend and ST segment elevation. Beginning at step 800, the implanted device evaluates ST segment elevation and ΔQTend. As before, if there is no substantial change in ST elevation, i.e. ST deviation is small, then the patient's condition is deemed to be normal, at step 802. If there has been a substantial change in ST elevation, then the device proceeds to determine whether there has also been a substantial change in QTend, i.e. whether ΔQTmax exceeds a threshold representative of a significant change. If not, then ischemia or hyperglycemia are suggested, at step 804, and further analysis may need to be performed to distinguish therebetween (such as by examining QTmax). If ΔQTend exceeds the threshold, however, the device then determines whether QTend has lengthened or shortened. If QTend has lengthened, then hypoglycemia is suggested that step 806. If QTend has instead become shorter, then the analysis is indeterminate, at step 808, perhaps indicative of erroneous data. As already explained, a significant change in ST segment elevation in combination with a significant change in QTend should be associated with lengthening of QTend, not a reduction in QTend. Accordingly, no warnings are issued.) Assuming the analysis is not indeterminate, appropriate warning signals are issued and therapy is adjusted.

In general, a wide variety of techniques can be implemented consistent with the principles the invention and no attempt is made herein to describe all possible techniques. Although described primarily with reference to an example wherein the implanted device is a defibrillation/pacer, principles of the invention are applicable to other implantable medical devices as well. In addition, whereas the techniques described herein are performed by the implanted device, the techniques may alternatively be performed by an external device using IEGM signals or other signals transmitted from the implanted device. For example, a bedside monitor may be configured to receive IEGM signals from the implanted device via "long-range" telemetry then analyze the signals using the aforementioned techniques and issue any appropriate warnings. Alternatively, the bedside monitor may transmit the IEGM data to a central server or other central processing device, which analyzes data from multiple patients to detect ischemia, hypoglycemia or hyperglycemia within any of those patients. In such an implementation, the central processing device then transmits appropriate warning signals to the bedside monitor of the patient for warning the patient and then additionally transmits appropriate warning signals to the physician associated with the patient or a third party such as emergency medical service (EMS) personnel. A system incorporating bedside monitoring units connected to a centralized system is described in U.S. Patent Application Serial Number 2002/0143372, of Snell et al., entitled "System and Method for Remote Programming of Implantable Cardiac Stimulation Devices," published Oct. 3, 2002.

Note that ischemia, hypoglycemia and hyperglycemia are not necessarily the only conditions that can cause changes in QTmax and/or QTend. As listed in Table I above, hyperkalemia and the use of digitals can potentially affect QTmax as well. More specifically, they tend to shorten both QTmax and QTend. Hence, the techniques discussed above can be extended to detect possible hyperkalemia within the patient. A physician may then confirm that hyperkalemia is indeed present (rather than merely the presence of digitalis.) Still other conditions and/or medications can potentially affect QTmax and QTend as well. For example, left ventricular hypertrophy (LVH), left bundle branch block (LBBB), benign early repolarization (BER), right bundle branch block (RBBB), left ventricular aneurysm, and acute pericarditis might have some affect on these parameters. Also, various medications can affect repolarization kinetics and hence can affect QTmax and QTend, though cardioactive drugs typically cause no significant deviation in either QTmax or QTend. Nevertheless, QTmax and QTend can be used to help corroborate detection of ischemia initially made based on ST segment deviation only. This is discussed in the following sections. Also, the techniques set forth in the above-cited patent to Boileau et al. may be used to identify changes, if any, within cardiac signals caused by medications, such that those changes can then be taken into account when detecting and distinguishing ischemia, hypoglycemia, hyperglycemia and hyperkalemia. Still further, at least some cardiological conditions that can potentially affect QTmax and QTend, such as LVH and BER, typically do not cause short-term changes in ST or T-wave parameters, and hence do not interfere with detection of ischemia, hypoglycemia, hyperglycemia and hyperkalemia based on relatively short-term variations in the ST or T-wave parameters, which is of primary importance. Furthermore, insofar as other conditions or medications (besides hypoglycemia) that might cause a lengthening of QT intervals, the techniques herein at least provide for detection of "systemic QT prolongation", permitting the physician to then diagnose the cause of the systemic prolongation.

Turning now to FIGS. 16-24, various systems and methods for efficiently detecting and distinguishing among cardiac ischemia, hypoglycemia, hyperglycemia and hyperkalemia will be described, which employ a two-tier detection procedure. Systems and methods for efficiently detecting and distinguishing AF are also described within this section.

Two-Tier Detection Techniques

Figure 16:
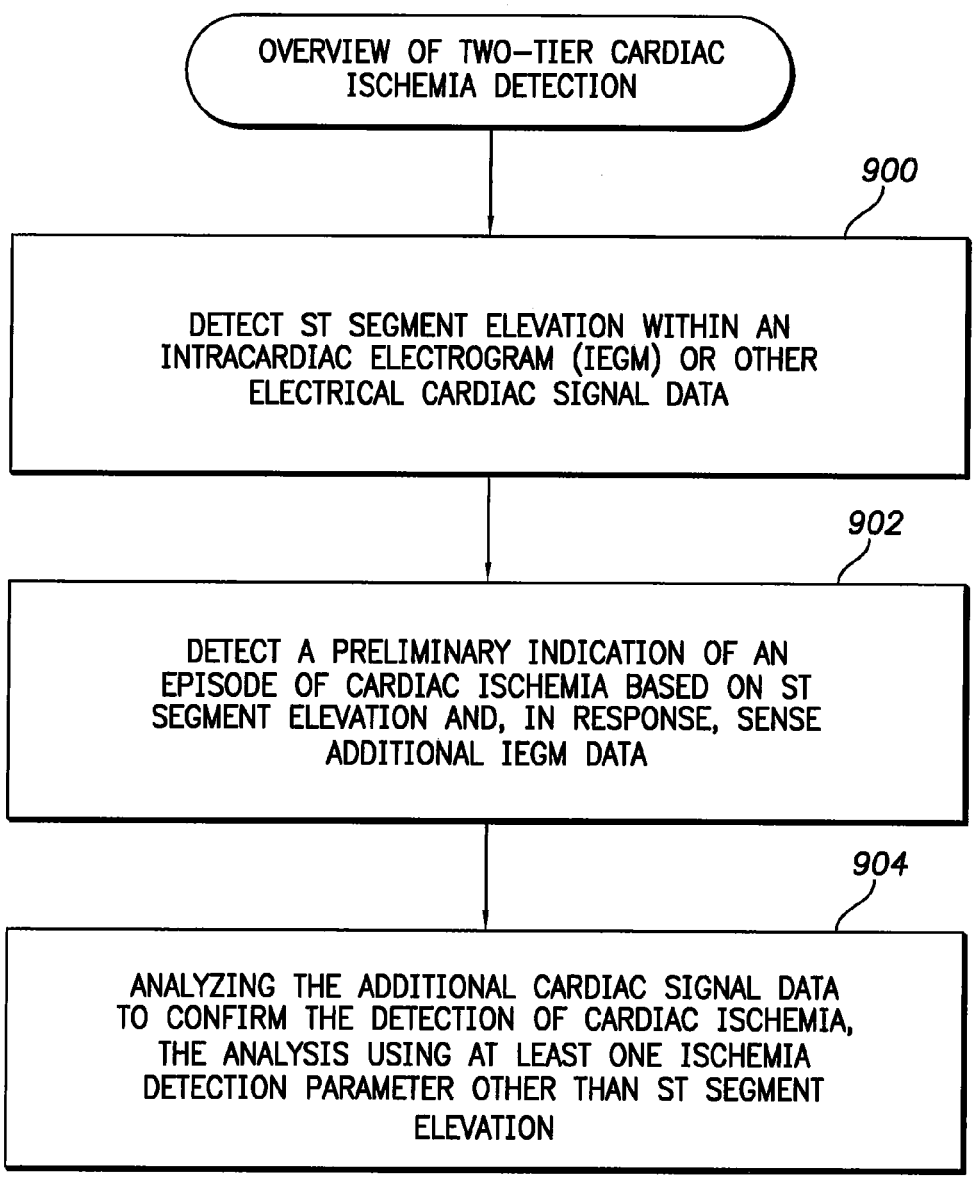
FIG. 16 is a flow chart providing an overview of an exemplary two-tier method performed by an implantable device, such as the device of FIG. 1, for efficiently detecting and confirming cardiac ischemia.

FIG. 16 provides an overview of a cardiac ischemia detection technique, which may be performed by an implanted device such as the pacer/ICD of FIG. 1. Initially, at step 900, IEGM signals are detected and ST elevations are measured by the implanted device. Then, at step 902, the implanted device detects a preliminary indication of an episode of cardiac ischemia based on ST segment elevation and, in response, senses additional IEGM data. In this regard, the implanted device can employ otherwise conventional ST segment elevation-based ischemia detection techniques to make the preliminary determination of cardiac ischemia. In one example, the amount of shift, if any, in ST segment elevation is measured and compared against a threshold indicative of possible cardiac ischemia. However, rather than immediately issuing warnings to the patient, the implanted device instead senses additional IEGM data (preferably at least four hour's worth) for use in confirming the detection of cardiac ischemia by, for example, using the techniques described above that exploit QTmax and QTend to distinguish among ischemia, hyperglycemia, hypoglycemia and hyperkalemia, each of which can affect ST segment elevation.

At step 904, the additional IEGM data is analyzed to, at the least, confirm or disconfirm the detection of cardiac ischemia and, preferably, to further detect hyperglycemia, hypoglycemia and hyperkalemia, if those conditions are instead present within the patient. The analysis of step 904 uses at least one ischemia detection parameter other than ST segment elevation, such as QTend and QTmax. As already explained, a decrease in QTmax along with little or no change in QTend tends to confirm the detection of cardiac ischemia. However, a lengthening of both QTmax and QTend indicates that the ST segment elevation shift was instead due to hypoglycemia. In contrast, a lack of change in both QTmax and QTend instead indicates that the ST segment elevation shift was instead due to hyperglycemia. A shortening of both QTmax and QTend is indicative of hyperkalemia (or the presence of digitalis.) Other parameters may be used as well to confirm or disconfirm the detection of cardiac ischemia, including post-T-wave-based detection parameters described in the above-referenced patent application to Wang et al. and T-wave energy-based parameters and T-wave slope-based parameters described in the above-referenced patent application Min et al. The ischemic burden techniques described above may also be exploited.

Thus, FIG. 16 provides an overview of a two-tiered technique wherein a preliminary indication of cardiac ischemia is made based on ST segment elevation and that preliminary indication is then confirmed or disconfirmed based on further analysis of additional data. Depending upon the implementation, the second stage of the procedure (i.e. step 904) can be implemented with the implanted device itself or can be implemented with an external device. Examples of each will be described below with reference to FIGS. 17-21. In either case, the implanted device need not initially perform the more sophisticated analysis involving, e.g., QTmax and QTend intervals, thus reducing the processing burden on the microprocessor of the device. Rather, the microprocessor need only evaluate ST segment elevations (typically once every thirty seconds) to monitor for possible cardiac ischemia. The more sophisticated analysis is initiated only if a significant ST shift is detected. Moreover, within implementations where the second stage of the analysis is performed by an external system, the microprocessor of the implanted device need not even be programmed to perform the more sophisticated analysis, thus reducing device programming complexity.

Figure 17:
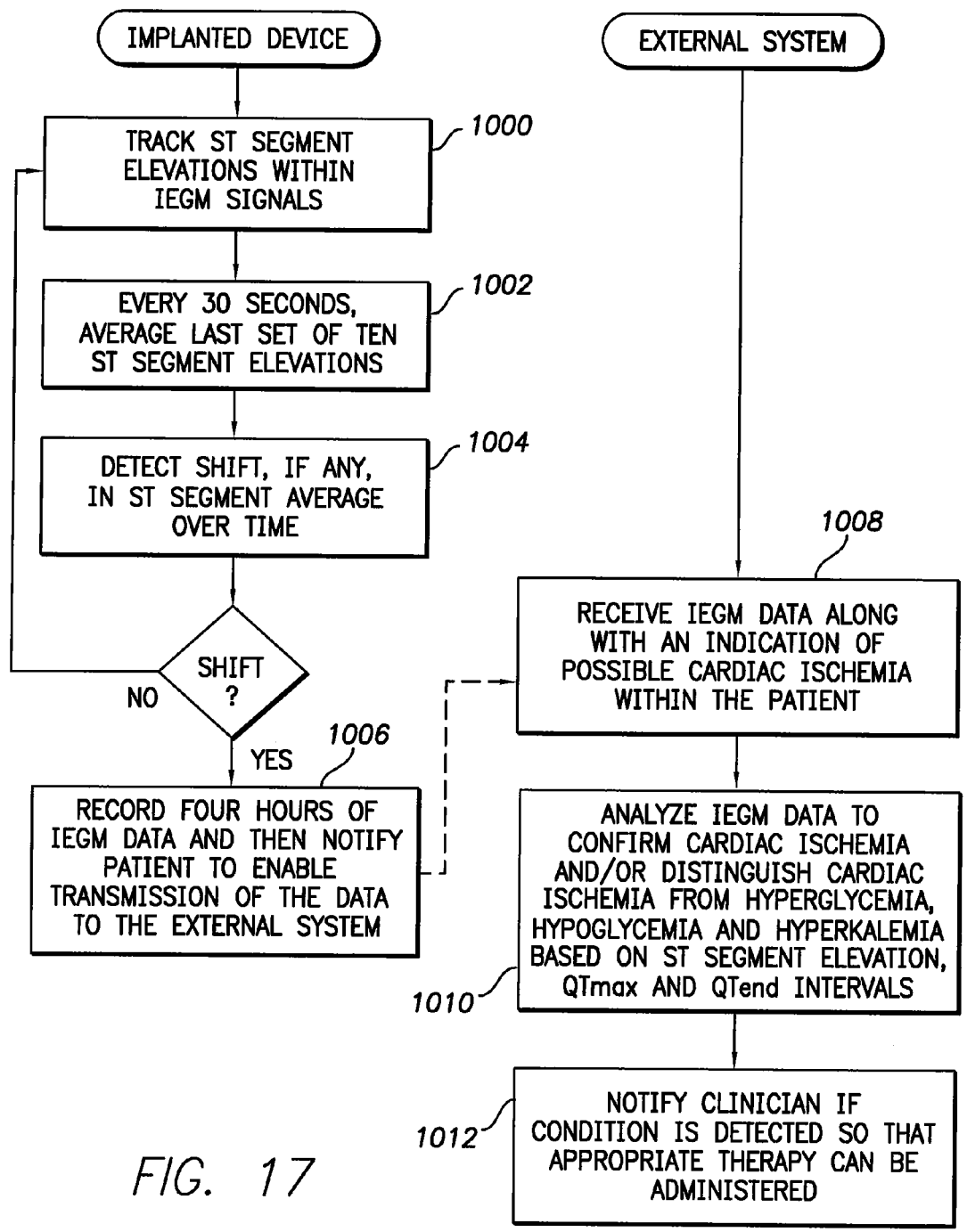
FIG. 17 is a flow chart summarizing an exemplary implementation of the two-tier method of FIG. 16 wherein confirmation of ischemia is performed by an external system.

FIG. 17 illustrates an example where the second stage of the analysis is performed by an external system, such as an external programmer (illustrated in FIG. 24), or a centralized processing device, such as is provided in conjunction with the St. Jude Medical HouseCall™ system. Beginning at step 1000, the implanted device tracks ST segment elevations within IEGM signals. At step 1002, once every 30 seconds, the implanted device averages the last set of ten ST segment elevations for comparison against previous ST segment elevation averages. The particular values of "30 seconds" and "ten segments" are, of course, merely exemplary. Preferably, the number of segments is kept fairly small (e.g. eight to sixteen segments) so as to minimize processing requirements. In any case, at step 1004, the implanted device detects a shift, if any, in ST segment elevation. For example, the device may calculate a difference between the current ST segment elevation average and a running average calculated based on previous sets of ST segment elevations. If the difference, i.e. the shift, exceeds a predetermined threshold, a preliminary indication of cardiac ischemia is thereby made. Step 1006 is then performed wherein the device senses and records a significant amount of additional IEGM data (typically about four hour's worth) for use in confirming the ischemia detection. The implanted device then notifies the patient to enable transmission of the data to the external system. Notification may be made using the above-described tickle warning devices or other suitable techniques. The patient, once notified, activates a HouseCall™ transmitter or other transtelephonic relay system, which relays the data to the external system. Transtelephonic relay devices and systems for networking such devices are set forth, for example, in U.S. Pat. No. 6,249,705 to Snell, entitled "Distributed Network System for use with Implantable Medical Devices". Alternatively, the patient may simply be notified to consult his or her physician, who will then use an external programmer to retrieve the additional stored data from the implanted device for analysis using the programmer. In yet another alternative, the physician uses the external programmer device to process real-time IEGM data, i.e. the programmer is not limited to processing IEGM previously recorded with the device. Rather the programmer can receive and process real-time IEGM data.

Beginning at step 1008, the external system performs the second stage of the two-tier procedure. That is, at step 1008, the external system receives the additional IEGM data along with an indication that the implanted device detected possible cardiac ischemia within the patient. At step 1010, the external system then analyzes the additional IEGM data to confirm cardiac ischemia and/or distinguish cardiac ischemia from other potential influences on the ST segment, such as hyperkalemia, hyperglycemia, and hypoglycemia based on ST segment elevation, QTmax and QTend intervals, and perhaps other non-ST-based parameters as well, such as post-T-wave-based parameters. In other words, the external system employs any or all of the techniques described above in connection with FIGS. 1-15 to detect and distinguish cardiac ischemia, hyperglycemia, hypoglycemia and hyperkalemia. These techniques will not be described again in detail here. Also, other non-ST segment-based detection techniques, not specifically described herein, may be used as well. Alternatively, implementations may be provided wherein the analysis performed by the external system uses only ST segment elevations, but performs a more sophisticated ST segment-based analysis than initially performed by the implanted system. In general, the second stage of the detection procedure employs any detection technique that has greater specificity than the detection procedure employed by the implanted device, which itself employs a technique having high sensitivity.

At step 1012, if a condition such as cardiac ischemia, hyperglycemia etc. is detected and/or confirmed, the external system notifies the patient's physician or other appropriate clinician so that appropriate therapy can be administered. Preferably, the system notifies the appropriate physician. For example, if the detected condition is cardiac ischemia, the system notifies a cardiologist, if the condition is hyperkalemia, the system notifies the appropriate specialist, etc. Typically, the physician then contacts the patient to schedule a follow-up session so that the physician may confirm the diagnosis and initiate appropriate therapy (such as a regime of prescriptive medications) or, if warranted, to reprogram pacing parameters of the implanted device within the patient. In some implementations, however, the external system is equipped to automatically send re-programming signals to the implanted device via the transtelephonic relay system to directly control or reprogram the implanted device. Such may be appropriate, for example, if the implanted device is equipped with implanted drug pumps or the like for directly dispensing appropriate medications (such as insulin in the case of hyperglycemia). As can be appreciated, a wide variety of therapeutic systems and techniques may be utilized and not all such systems and techniques can be fully described here. Note also that, if the analysis performed by the external system concludes the patient does not have cardiac ischemia, hyperglycemia, hypoglycemia or hyperkalemia, then, preferably, an appropriate notification is sent back to the patient so that he or she may be appropriately advised.

Figure 18:
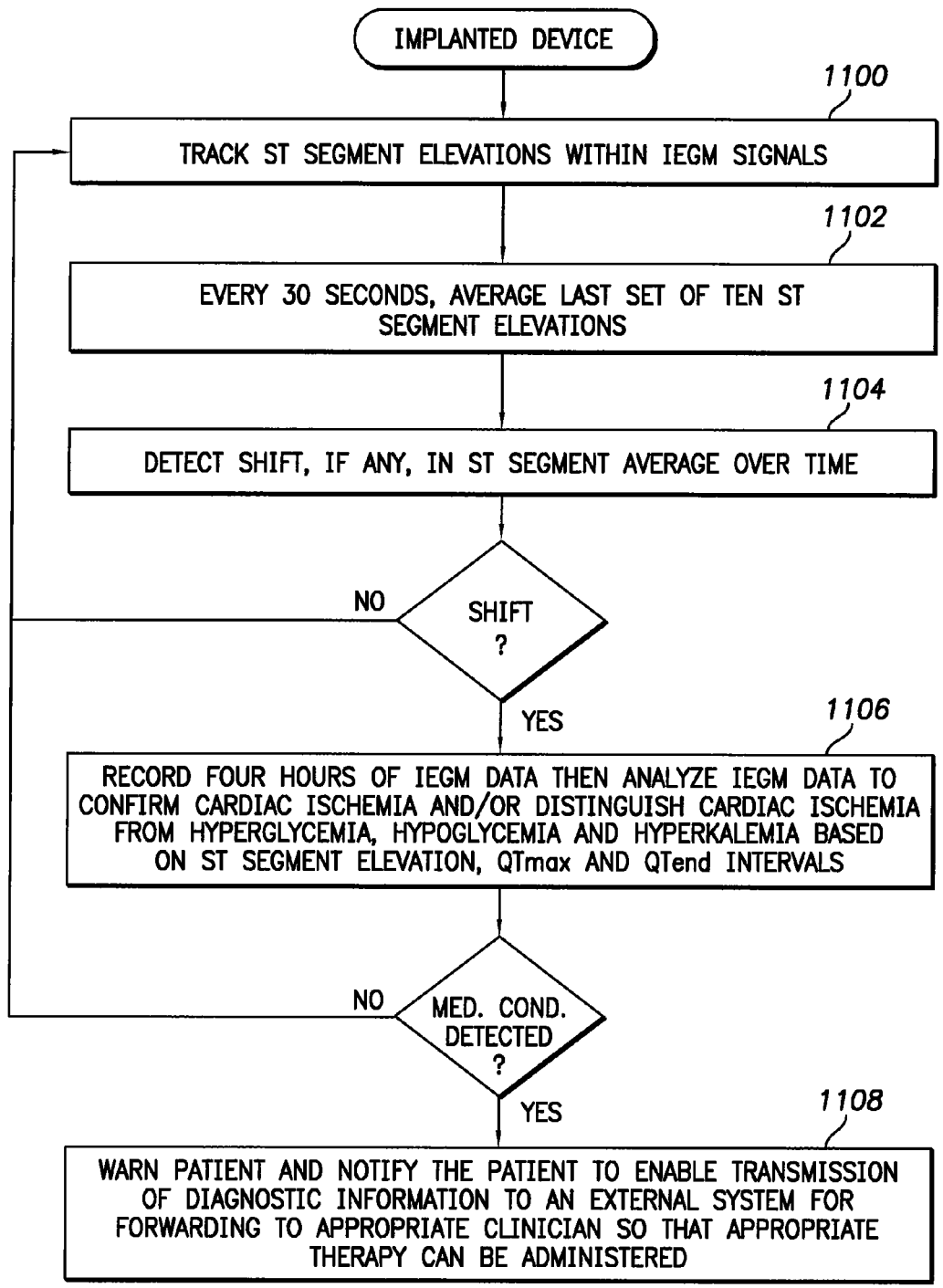
FIG. 18 is a flow chart summarizing an exemplary implementation of the two-tier method of FIG. 16 wherein confirmation of ischemia is performed by the implanted device itself.

FIG. 18 illustrates an example where the second stage of the analysis is performed by the implanted device itself. Many of the steps of FIG. 18 are the same or similar to steps of FIG. 17 and will not be described again in any detail. Steps 1100, 1102 and 1104 are initially performed to track ST segment elevations and detect a shift, if any, in ST segment elevation. If a significant shift is detected, the device, at step 1106, senses and records four hours of additional IEGM data for use in confirming the ischemia detection and/or distinguishing cardiac ischemia from hyperglycemia, hypoglycemia and hyperkalemia based on ST segment elevation, QTmax and QTend intervals. If such a medical condition is confirmed, then, at step 1108, the device warns the patient and notifies the patient to initiate transmission of diagnostic information to an external system (such as the centralized HouseCall™ processing system) for notifying the patient's physician or other clinician so that appropriate therapy can be administered. Alternatively, if so equipped, the implant device can automatically administer appropriate therapy, such as by controlling an implanted drug pump to deliver appropriate medications.

Figure 19:
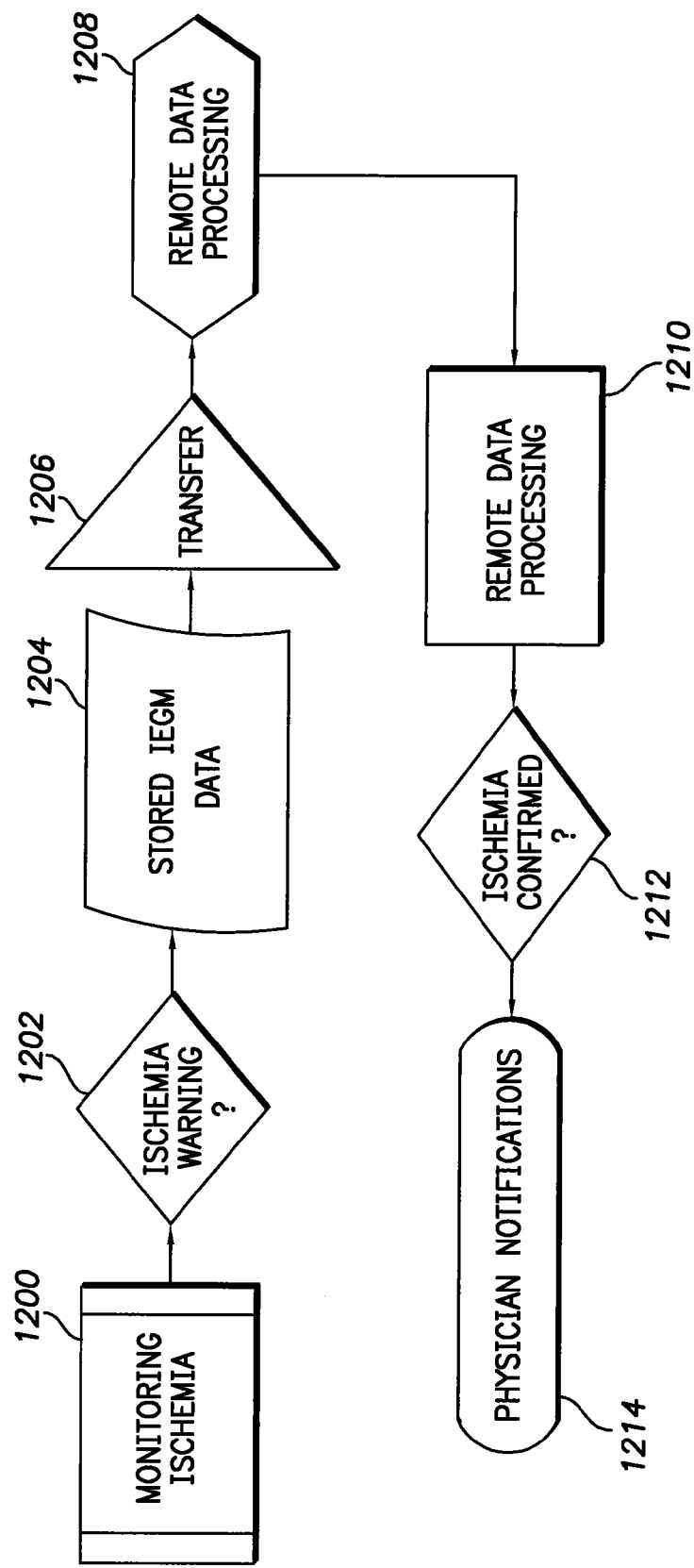
FIG. 19 is a schematic illustration of pertinent functional components/steps of a system for implementing the method of FIG. 17.
Figure 20:
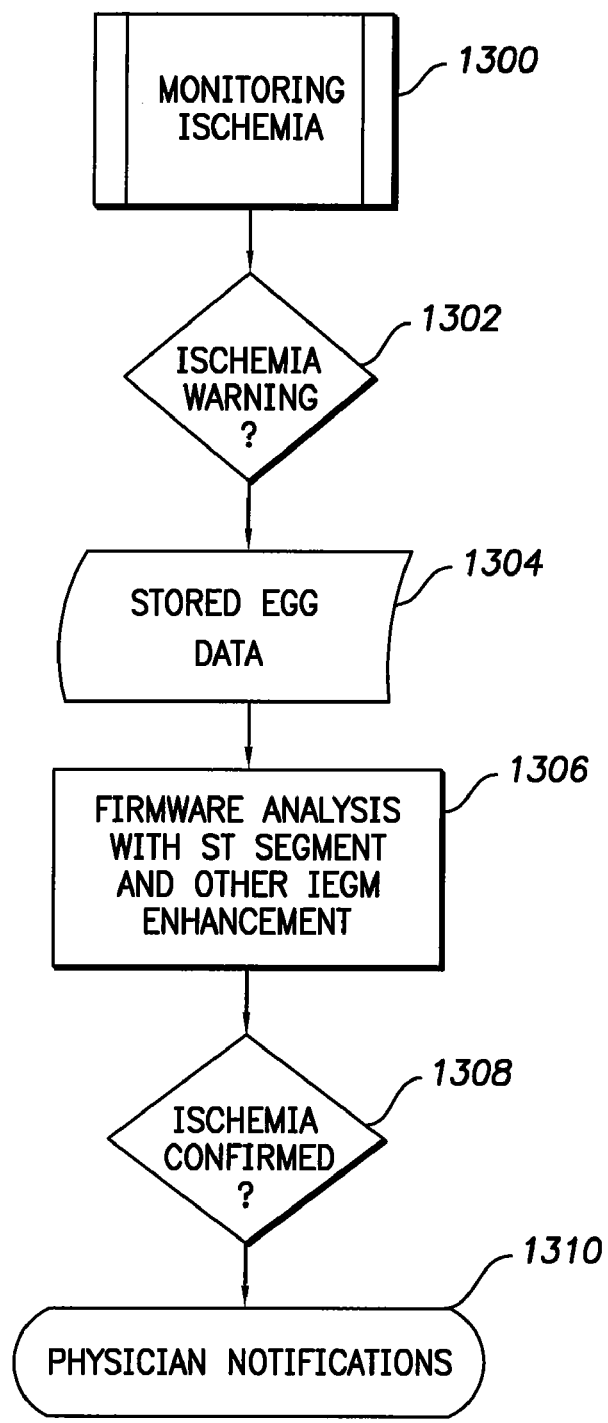
FIG. 20 is a schematic illustration of pertinent functional components/steps of a system for implementing the method of FIG. 18.

FIGS. 19 and 20 provide an alternative illustration of the systems and techniques of FIGS. 17 and 18, respectively, which serve to highlight functional components/steps. Briefly, within FIG. 19, ischemia is monitored, at block 1200, by the implanted device using a relatively simple detection technique such as ST segment shift. An ischemia warning, at block 1202, triggers storage of additional IEGM data within database 1204. The additional data is transferred at block 1206 to a remote data processing unit 1208, which may by a device programmer, centralized processor or other appropriate external system. Remote processing is performed at block 1210 to, at least, confirm detection of ischemia. If confirmed, at block 1212, the physician is notified, block 1214. Within FIG. 20, ischemia is again monitored, at block 1300, by the implanted device using a relatively simple detection technique. An ischemia warning, at block 1302, triggers storage of additional IEGM data within database 1304. The additional data is analyzed by firmware within the device itself at block 1306 to, at least, confirm detection of ischemia. If confirmed, at block 1308, the physician is notified, block 1310 via appropriate transmission, not separately shown.

Figure 21:
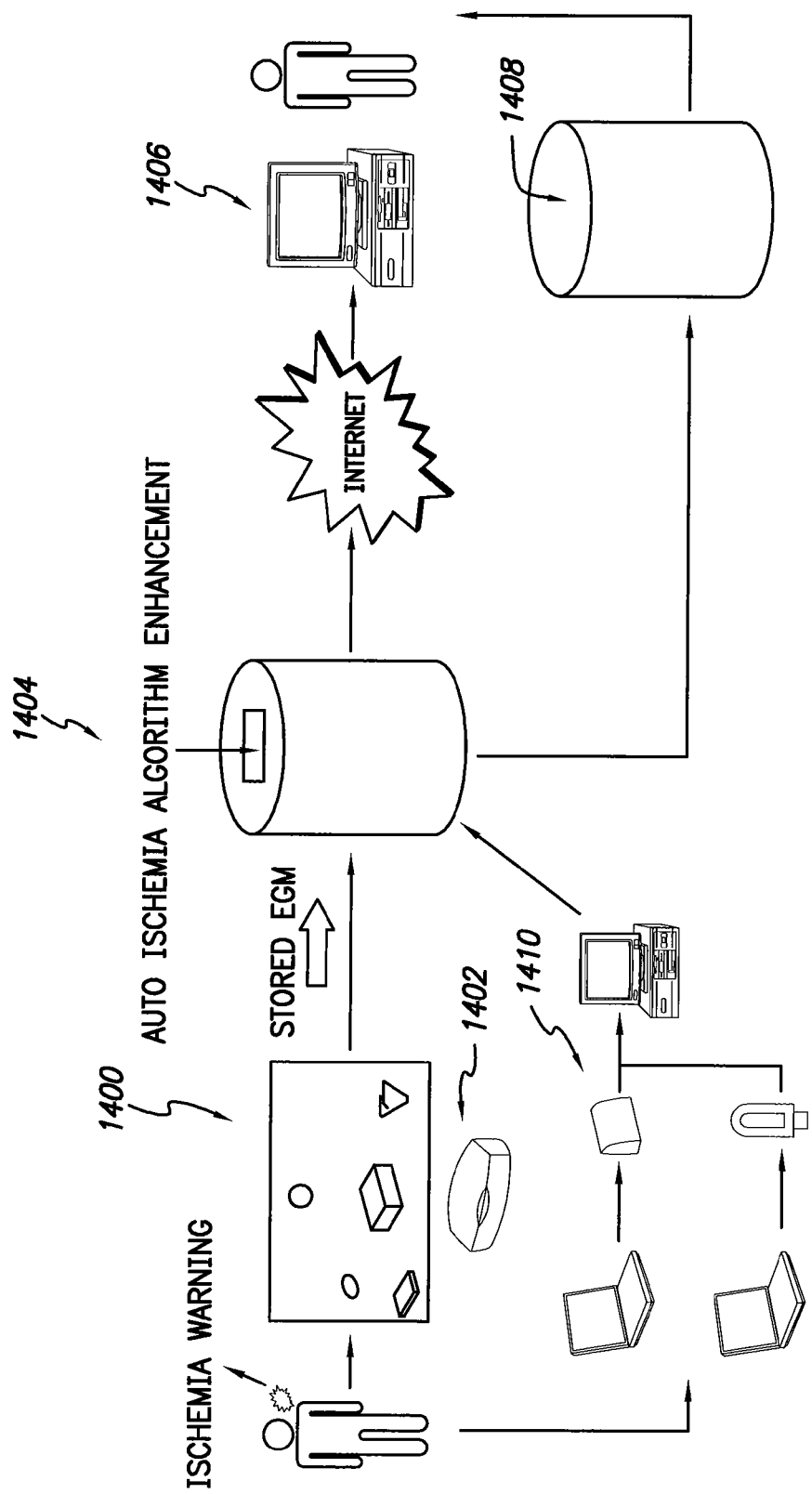
FIG. 21 illustrates an overall system for implementing the methods of FIG. 17.

FIG. 21 illustrates an overall system for implementing the various techniques of FIGS. 16-20, which includes various alternative external data processing components. Following a preliminary ischemia detection made by the implanted device itself, IEGM data for further analysis may be sent via a home data hub 1400 or a HouseCall™ monitor 1402 to a centralized server 1404, which performs the second stage of the analysis using ischemia algorithm enhancements, i.e. using additional detection parameter besides ST segment elevation such as QTmax and QTend. If ischemia is confirmed, appropriate notifications are sent via the Internet to a physician computer 1406 so as to notify the physician. In particular, a portable document format (PDF) file containing a report of the analysis of the patient IEGM data including key data elements may be sent via a service provider server 1408 to the physician. Additionally, a device programmer system 1410 may be provided for performing real-time analysis of patient IEGM data using the enhanced ischemia detection techniques. Data and reports generated by the programmer device may also be stored on the centralized server 1404.

Figure 22:
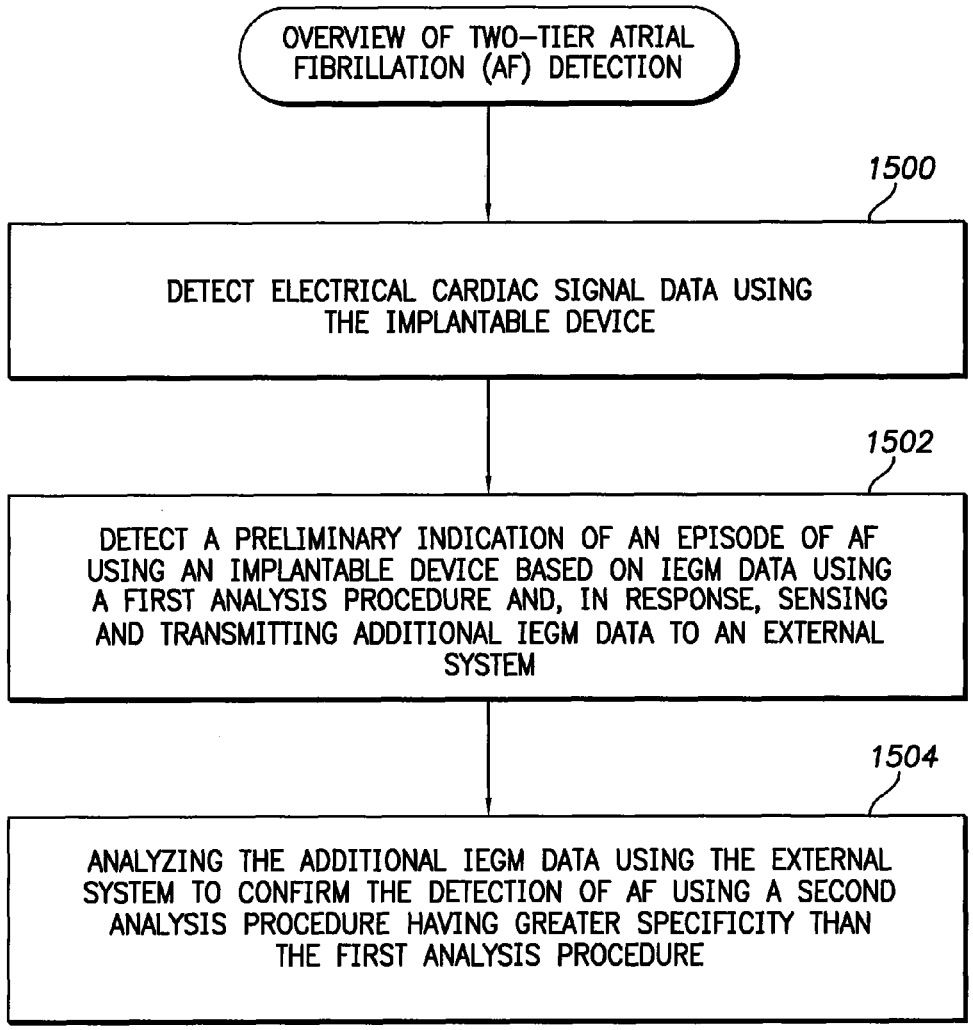
FIG. 22 is a flow chart providing an overview of an exemplary two-tier method for detecting AF performed by an implantable device, such as the device of FIG. 1, along with an external device.

The two-tier detection and confirmation techniques of the invention are not limited to just detecting cardiac ischemia, hypoglycemia and hyperglycemia, but may be applied to other conditions as well. FIG. 22 summarizes an implementation where the two-tier technique is applied to the detection of AF. At step 1500, IEGM signals are detected using an implanted device. Then, at step 1502, the implanted device detects a preliminary indication of an episode of AF based on the IEGM data using a first, relatively simple, analysis procedure and in response, senses and records additional IEGM data for further analysis. In this regard, the implanted device can simply assess the atrial rate based on IEGM signal and make a preliminary determination of AF, if the atrial rate exceeds a predetermined threshold. The implanted device then senses and transmits the additional IEGM data (preferably at least four hour's worth) to an external system for use in confirming the detection of AF, such as an external programmer or centralized programming device. At step 1504, the additional IEGM data is analyzed by the external device to confirm or disconfirm the detection of AF.

The analysis of step 1504 uses a more sophisticated analysis technique than employed by the implanted device, such as techniques that employ beat classification or that analyze the morphology of the atrial IEGM signal. See, for example, techniques described in U.S. Patent Application 2002/0143266 of Bock, entitled "Atrial Fibrillation Detection Method and Apparatus" and in U.S. Pat. No. 5,400,795 to Murphy, et al., entitled "Method of Classifying Heart Rhythms by Analyzing Several Morphology Defining Metrics Derived for a Patient's QRS Complex". See also, U.S. Pat. No. 7,076,300 to Kroll, et al., entitled "Implantable Cardiac Stimulation Device and Method that Discriminates Between and Treats Atrial Tachycardia and Atrial Fibrillation" and U.S. Pat. No. 5,720,295 to Greenhut, et al., entitled "Pacemaker with Improved Detection of Atrial Fibrillation". The two-tier AF detection technique of FIG. 22 is particularly well suited for use in managing critical AF patients post-ablation or post-cardioversion. The managing clinician may want to know if the patient is having recurrent AF before putting the patient on coumadin therapy, instituting new anti-arrhythmic drug therapy or performing further ablation. It is especially important to have a sensitive automatic assessment of AF because very often the patient is unaware of their AF.

Figure 23:
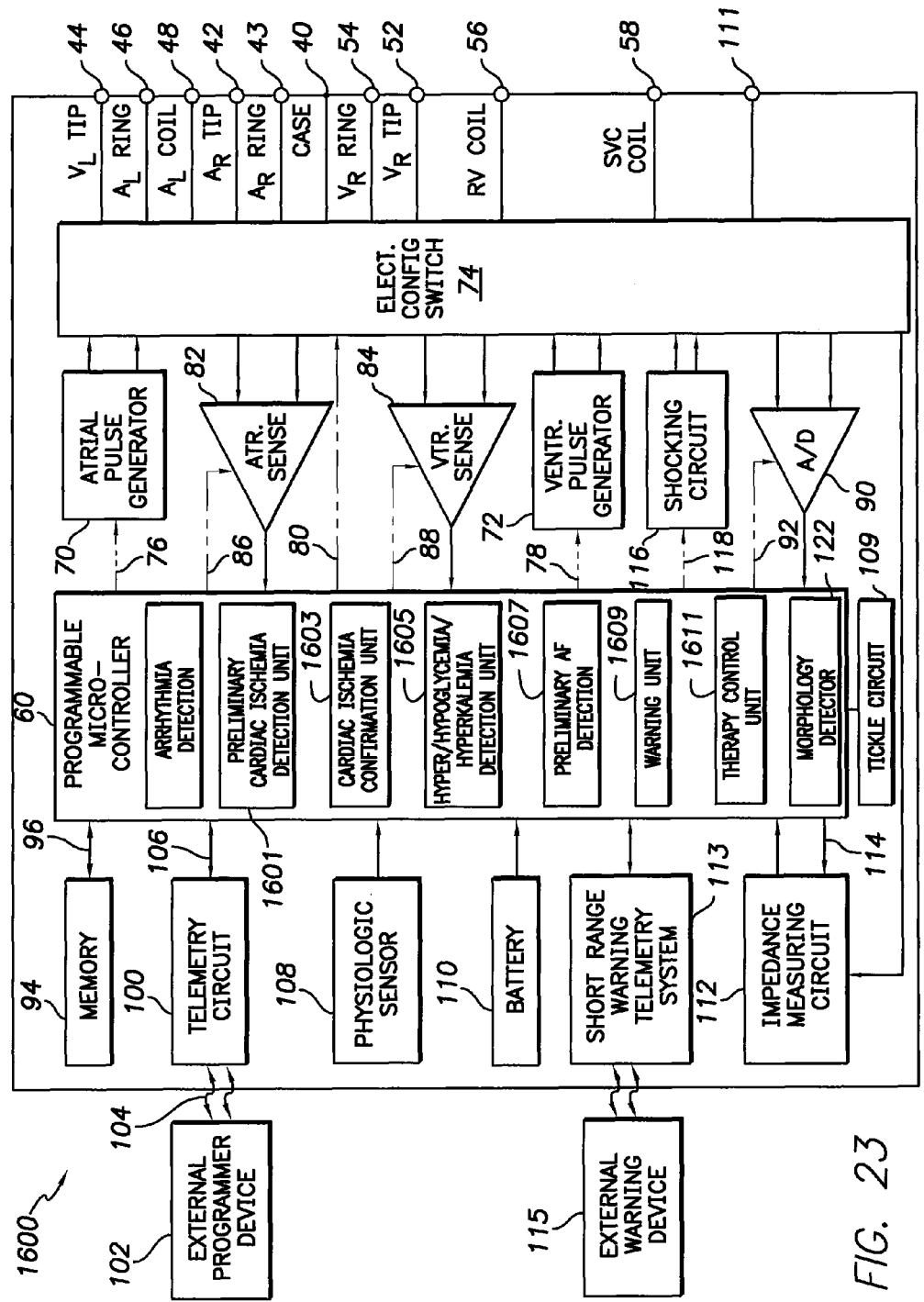
FIG. 23 is a functional block diagram of an exemplary implementation of the device of FIG. 1 equipped to implement the techniques of FIGS. 16-22.
Figure 24:
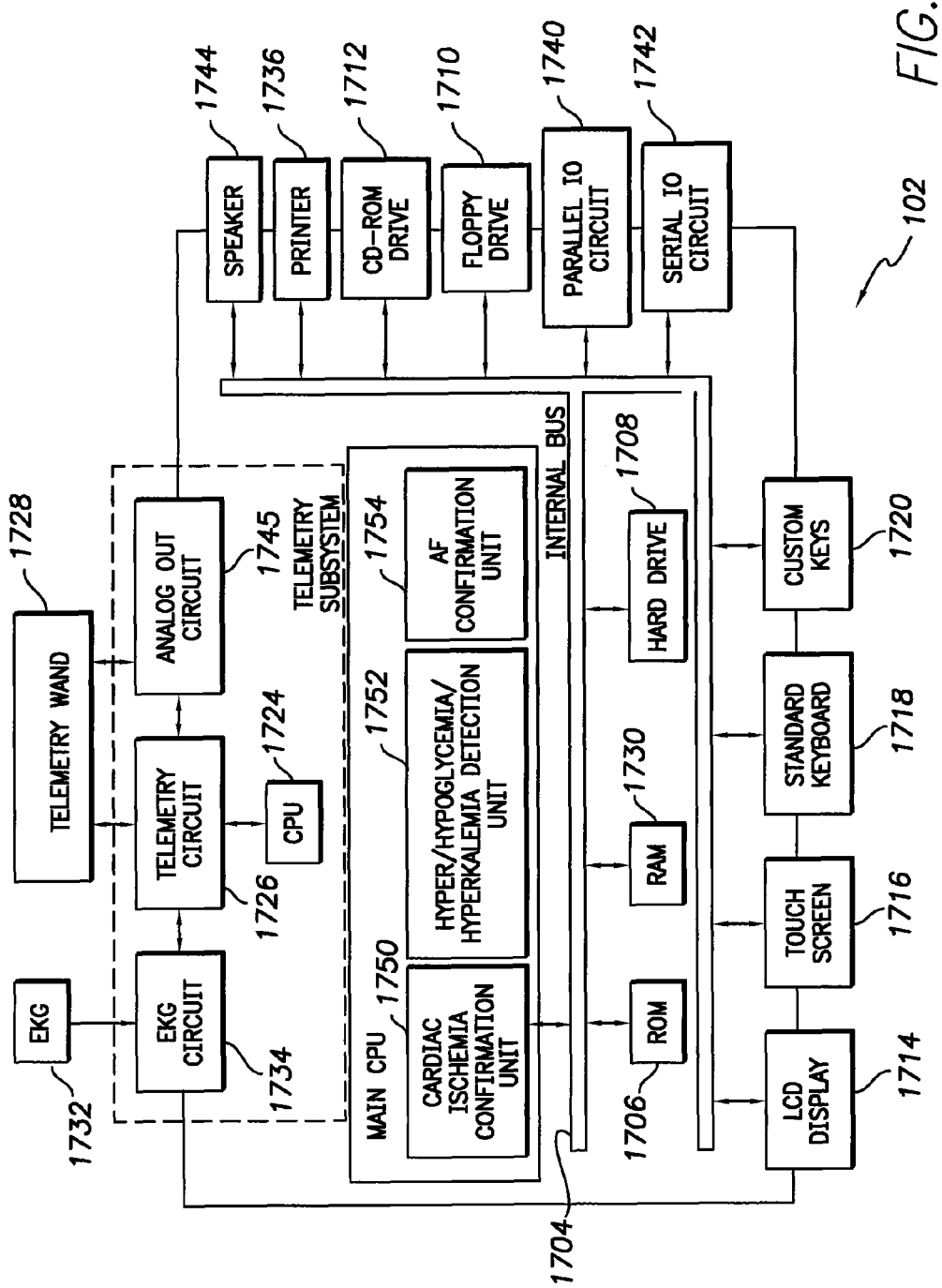
FIG. 24 is a functional block diagram illustrating components of a device programmer of FIG. 23, and in particular illustrating a programmer-based ischemia confirmation system and a programmer-based AF confirmation system.

Turning now to FIGS. 23-24, exemplary implementations of an implanted device and an external programmer will be described, which include components for performing the various techniques of FIGS. 16-22. Referring first to FIG. 23, pertinent components of an implanted device 1600 are illustrated. Device 1600 is similar to the device of FIG. 2 and most components retain their previous reference numerals. These components will not be redescribed. Additionally, however, the microprocessor of device 1600 of FIG. 23 includes a preliminary cardiac ischemia detection unit 1601 operative to detect a preliminary indication of an episode of cardiac ischemia based on ST segment elevation and, in response, to control the recording of additional cardiac signal data (within memory 94) for further analysis. (Although not shown, the microprocessor also includes an ST segment elevation detector for actually detecting ST segment elevation within electrical cardiac signal data.) In the example of FIG. 23, the microprocessor also includes a cardiac ischemia confirmation unit 1603 operative to analyze the additional cardiac signal data to confirm the detection of cardiac ischemia in accordance with the techniques of FIG. 18. That is, in this example, the device is equipped to perform the confirmation stage of the two-tier analysis procedure. As already explained, confirmation employs at least one ischemia detection parameter other than ST segment elevation, such as QTmax or QTend.

In the example of FIG. 23, a hyper/hypoglycemia/hyperkalemia detection unit 1605 is also provided, which is capable of detecting hyperglycemia and/or hypoglycemia, if cardiac ischemia is disconfirmed. Together, ischemia confirmation unit 1603 and hyper/hypoglycemia detection unit 1605 allow the device to distinguish among cardiac ischemia, hyperglycemia, and hypoglycemia. Note that, within implementations where the external device instead performs the additional analysis to confirm cardiac ischemia (such as in the technique of FIG. 17), the cardiac ischemia confirmation unit 1603 and hyper/hypoglycemia detection unit 1605 are not required within the implanted device. Indeed, in such implementations, it is preferred that those components are not implemented within the implanted device, thereby reducing the complexity of the microprocessor and/or its programming. Also, note that if an ischemia confirmation unit and a hyper/hypoglycemia detection unit are provided within the implanted device, these components may be implemented as firmware separate from the microprocessor.

In the example of FIG. 23, the microprocessor of device 1600 also includes a preliminary AF detection unit 1607 operative to detect a preliminary indication of an episode of AF based on IEGM data using a first analysis procedure, such as a simple atrial rate-based detection procedure. If AF is detected, the AF detection unit 1607 controls the transmission of additional IEGM data to an external system (such as programmer device 102) for analysis therein in accordance with the techniques of FIG. 22. A warning unit 1609 controls the generation of warning signals for notifying the patient of possible ischemia and/or AF using, e.g., tickle warning circuit 109. Also, a therapy control unit 1611 is provided for controlling any therapy to be directly applied to the patient by the device in response to a medical condition, such as in response to cardiac ischemia.

Alternatively, the implantable device may be a loop recorder, i.e. an implantable device equipped to passively detect a subcutaneous electrocardiogram (ECG).

Exemplary External Programmer

FIG. 24 illustrates pertinent components of an external programmer 102 for use in programming pacer/ICD 1600 of FIG. 23 and for performing the above-described cardiac ischemia confirmation and AF confirmation techniques if the pacer/ICD is not equipped to perform those techniques itself. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 102 may also be capable of processing and analyzing data received from the implanted device and from the EKG leads to, for example, render preliminary diagnosis as to medical conditions of the patient or to the operations of the implanted device.

Now, considering the components of programmer 102, operations of the programmer are controlled by a CPU 1702, which may be a generally programmable microprocessor or microcontroller or may be a dedicated processing device such as an application specific integrated circuit (ASIC) or the like. Software instructions to be performed by the CPU are accessed via an internal bus 1704 from a read only memory (ROM) 1706 and random access memory 1730. Additional software may be accessed from a hard drive 1708, floppy drive 1710, and CD ROM drive 1712, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 1714 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 1716 overlaid on the LCD display or through a standard keyboard 1718 supplemented by additional custom keys 1720, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 102 to retrieve data stored within any implanted devices and to also retrieve EKG data from EKG leads, if any, coupled to the patient. To this end, CPU 1702 transmits appropriate signals to a telemetry subsystem 1722, which provides components for directly interfacing with the implanted devices, and the EKG leads. Telemetry subsystem 1722 includes its own separate CPU 1724 for coordinating the operations of the telemetry subsystem. Main CPU 1702 of programmer communicates with telemetry subsystem CPU 1724 via internal bus 1704. Telemetry subsystem additionally includes a telemetry circuit 1726 connected to telemetry wand 1728, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 1734 for receiving surface EKG signals from a surface EKG system 1732. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 102 either within a random access memory (RAM) 1730, hard drive 1708 or within a floppy diskette placed within floppy drive 1710. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 102, the implanted devices may be further controlled to transmit additional data in real time as it is detected by the implanted devices, such as additional IEGM data, lead impedance data, and the like. Additionally, or in the alternative, telemetry subsystem 1722 receives EKG signals from EKG leads 1732 via an EKG processing circuit 1734. As with data retrieved from the implanted device itself, signals received from the EKG leads are stored within one or more of the storage devices of the external programmer. Typically, EKG leads output analog electrical signals representative of the EKG. Accordingly, EKG circuit 1734 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 1702, the programming commands are converted to specific programmable parameters for transmission to the implanted devices via telemetry wand 1728 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 1736.

Additionally, CPU 1702 also preferably includes a cardiac ischemia confirmation unit 1750 operative to confirm a preliminary detection of cardiac ischemia made by the implanted device based on additional IEGM data sent from the device to the programmer, either in real-time or using previously recorded data. That is ischemia confirmation unit 1750 performs the second-tier of the ischemia detection procedure wherein parameters addition to ST segment elevation, such as QTend and QTmax are employed. A hyper/hypoglycemia/hyperkalemia detection unit 1752 is also provided to detect hyperglycemia or hypoglycemia based on ST segment elevation, QTend and QTmax. Together, ischemia confirmation unit 1750 and hyper/hypoglycemia detection unit 1752 permit the external programmer to distinguish among cardiac ischemia, hyperglycemia and hypoglycemia. CPU 1702 also includes an AF confirmation unit 1754 operative to confirm a preliminary detection of AF made by the implanted device using techniques described primarily with reference to FIG. 22.

Programmer/monitor 102 also includes a modem 1738 to permit direct transmission of data to other programmers via the public switched telephone network (PSTN) or other interconnection line, such as a T1 line or fiber optic cable. Depending upon the implementation, the modem may be connected directly to internal bus 1704 may be connected to the internal bus via either a parallel port 1740 or a serial port 1742. Other peripheral devices may be connected to the external programmer via parallel port 1740 or a serial port 1742 as well. Although one of each is shown, a plurality of input output (IO) ports might be provided. A speaker 1744 is included for providing audible tones to the user, such as a warning beep in the event improper input is provided by the physician. Telemetry subsystem 1722 additionally includes an analog output circuit 1745 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 24 are intended merely to provide an overview of the operation of programmer and are not intended to describe in detail every feature of the hardware and software of the programmer and is not intended to provide an exhaustive list of the functions performed by the programmer.

The various functional components of the exemplary systems described herein may be implemented using any appropriate technology including, for example, microprocessors running software programs or ASICs executing hard-wired logic operations. The exemplary embodiments of the invention described herein are merely illustrative of the invention and should not be construed as limiting the scope of the invention.

What is claimed is:

1. A method for use with an implantable medical device for detecting cardiac ischemia within a patient in which the device is implanted, the method comprising:

detecting ST segment elevation within electrical cardiac signal data;

detecting a preliminary indication of an episode of cardiac ischemia based on ST segment elevation and, in response, sensing additional electrical cardiac signal data;

detecting QTmax intervals and QTend intervals within the additional data;

analyzing the QTmax intervals and the QTend intervals to detect for changes in QTmax intervals and changes in QTend intervals, wherein said changes in QTmax intervals and QTend intervals include lengthening or decreases in said intervals; and confirming the episode of cardiac ischemia based on the combination of a decrease in the QTmax intervals and a lack of significant change in the QTend intervals, or distinguishing among cardiac ischemia and other potential causes of ST segment deviation based on other changes in the QTmax intervals and the QTend intervals.

2. The method of claim 1 wherein analyzing the QTmax intervals and QTend intervals to confirm the detection of cardiac ischemia is performed using a system external to the patient following transmission of the additional electrical cardiac signal data from the implanted device to the external system.

3. The method of claim 2 further including forwarding a notification of the medical condition from the external system to a medical professional.

4. The method of claim 2 wherein the external system includes a centralized processor and a transtelephonic relay device and wherein the transtelephonic relay device relays the additional electrical cardiac signal data from the implanted device of the patient to the centralized processor.

5. The method of claim 1 wherein analyzing the QTmax intervals and QTend intervals and confirming the episode of cardiac ischemia is performed by the implantable device itself.

6. The method of claim 1 wherein the ST segments are representative of intervals between the ends of depolarization events (QRS-complexes) and the beginnings of corresponding repolarization events (T-waves).

7. The method of claim 1 wherein detecting a preliminary indication of an episode of cardiac ischemia based on ST segment elevation includes detecting a shift in ST segment elevation based on a predetermined number of heartbeats.

8. The method of claim 1 wherein analyzing the QTmax intervals and QTend intervals and confirming the episode of cardiac ischemia include analyzing QTmax intervals and QTend intervals recorded during a predetermined period of time.

9. The method of claim 8 wherein the predetermined period of time for confirming the episode of cardiac ischemia is at least four hours.

10. The method of claim 1 wherein:
QTmax intervals are representative of intervals between the start of depolarization events and the peaks of corresponding repolarization events; and
QTend intervals are representative of intervals between the start of depolarization events and the ends of corresponding repolarization events.

11. The method of claim 1 wherein distinguishing among cardiac ischemia and other potential causes of ST segment deviation includes:
distinguishing an episode of hypoglycemia or other systemic QT prolongation condition from cardiac ischemia based on a significant lengthening of one or more of QTmax intervals and QTend intervals.

12. The method of claim 1 wherein distinguishing among cardiac ischemia and other potential causes of ST segment deviation includes
distinguishing an episode of hyperglycemia from cardiac ischemia based on a significant change in ST segment elevation in combination with a lack of significant change in both the QTend intervals and the QTmax intervals.

13. The method of claim 1 wherein distinguishing among cardiac ischemia and other potential causes of ST segment deviation includes
distinguishing an episode of hyperkalemia from cardiac ischemia based on a significant change in ST segment elevation in combination with a significant decrease in both the QTend intervals and the QTmax intervals.

14. The method of claim 1 further including the step of generating a warning signal in response to detection of a preliminary indication of cardiac ischemia.

15. A system for detecting cardiac ischemia within a patient, the system comprising:
an implantable medical device comprising:
a data acquisition system configured to acquire electrical cardiac signal data;
memory configured to record electrical cardiac signal data;
an ST segment elevation detector operative to detect ST segment elevation within electrical cardiac signal data; and
a cardiac ischemia detector operative to detect a preliminary indication of an episode of cardiac ischemia based on ST segment elevation and, in response, further operative to control the recording of additional cardiac signal data; and
a cardiac ischemia confirmation system operative to detect QTmax intervals and QTend intervals within the additional data; analyze the QTmax intervals and the QTend intervals to detect for changes in QTmax intervals and changes in QTend intervals, wherein said changes in QTmax intervals and QTend intervals include lengthening or decreases in said intervals; and
confirm the episode of cardiac ischemia based on the combination of a decrease in the QTmax intervals and a lack of significant change in the QTend intervals, or distinguish among cardiac ischemia and other potential causes of ST segment deviation based on other changes in the QTmax intervals and the QTend intervals.

16. The system of claim 15 wherein the cardiac ischemia confirmation system is a component of the implanted device.

17. The system of claim 15 wherein the cardiac ischemia confirmation system is a component of a device external to the patient.

18. A system for use with an implantable medical device for detecting and distinguishing certain medical conditions within a patient in which the device is implanted, the system comprising:
means for detecting ST segment elevation within electrical cardiac signal data;
means for detecting a preliminary indication of an episode of cardiac ischemia based on ST segment elevation and, in response, for controlling the recording of additional electrical cardiac signal data;
means for detecting QTmax intervals and QTend intervals within the additional data:
means for analyzing the QTmax intervals and the QTend intervals to detect for changes in QTmax intervals and changes in QTend intervals, wherein said changes in QTmax intervals and QTend intervals include lengthening or decreases in said intervals; and
means for confirming the episode of cardiac ischemia based on the combination of a decrease in the QTmax intervals and a lack of significant change in the QTend intervals, or distinguishing among cardiac ischemia and hypoglycemia, hyperglycemia and hyperkalemia based on other changes in the QTmax intervals and the QTend intervals.

* * * * *